US007001617B2

(12) United States Patent
Burrell et al.

(10) Patent No.: US 7,001,617 B2
(45) Date of Patent: Feb. 21, 2006

(54) METHOD OF INDUCTION OF APOPTOSIS AND INHIBITION OF MATRIX METALLOPROTEINASES USING ANTIMICROBIAL METALS

(75) Inventors: Robert Edward Burrell, Sherwood Park (CA); John Barrymore Wright, San Antonio, TX (US); Kan Lam, San Antonio, TX (US)

(73) Assignee: Nueryst Pharmaceuticals Corp., Fort Saskatchewan (CA)

( * ) Notice: Subject to any disclaimer, the term of this patent is extended or adjusted under 35 U.S.C. 154(b) by 55 days.

(21) Appl. No.: 10/159,587

(22) Filed: May 30, 2002

(65) Prior Publication Data

US 2003/0072810 A1 Apr. 17, 2003

Related U.S. Application Data

(63) Continuation-in-part of application No. 10/131,511, filed on Apr. 23, 2002, now Pat. No. 6,939,568, and a continuation-in-part of application No. 10/131,509, filed on Apr. 23, 2002, and a continuation-in-part of application No. 10/128,208, filed on Apr. 23, 2002, and a continuation-in-part of application No. 10/131,568, filed on Apr. 23, 2002, which is a continuation-in-part of application No. 09/840,637, filed on Apr. 23, 2001.

(60) Provisional application No. 60/285,884, filed on Apr. 23, 2001.

(51) Int. Cl.
*A61K 9/14* (2006.01)
*A61K 31/28* (2006.01)
*A61K 33/24* (2006.01)
*A61K 33/38* (2006.01)
*A61P 19/00* (2006.01)

(52) U.S. Cl. ............ 424/618; 424/400; 424/402; 424/404; 424/405; 424/443; 424/445; 424/447; 424/489; 424/490; 424/619; 424/646; 424/649; 514/492; 514/495; 514/825; 514/878; 514/951; 514/964

(58) Field of Classification Search ........ 424/618–619, 424/487, 489, 400, 402, 404–405, 490, 646, 424/649, 443, 445, 447; 514/492, 495, 825, 514/878, 951, 964
See application file for complete search history.

(56) References Cited

U.S. PATENT DOCUMENTS

| | | | |
|---|---|---|---|
| 3,757,786 A | 9/1973 | Smith | |
| 3,800,792 A | 4/1974 | McKnight et al. | |
| 3,918,446 A | 11/1975 | Buttaravoli | |
| 4,059,105 A | 11/1977 | Citruzzula et al. | |
| 4,324,237 A | 4/1982 | Buttaravoli | |
| 4,355,636 A | 10/1982 | Oetjen et al. | |
| 4,476,590 A | 10/1984 | Scales et al. | |
| 4,581,028 A | 4/1986 | Fox, Jr. et al. | |
| 4,596,556 A | 6/1986 | Morrow et al. | |
| 4,633,863 A | 1/1987 | Filips et al. | |
| 4,749,572 A | 6/1988 | Ahari | |
| 4,790,824 A | 12/1988 | Morrow et al. | |
| 4,803,066 A | 2/1989 | Edwards | |
| 4,828,832 A | 5/1989 | De Cuellar et al. | |
| 4,847,049 A | 7/1989 | Yamamoto | |
| 4,952,411 A | 8/1990 | Fox, Jr. et al. | |
| 4,960,413 A | 10/1990 | Sagar et al. | |
| 5,019,096 A | 5/1991 | Fox, Jr. et al. | |
| 5,064,413 A | 11/1991 | McKinnon et al. | |
| 5,122,418 A | 6/1992 | Nakane et al. | |
| 5,143,717 A | 9/1992 | Davis | |
| 5,236,421 A | 8/1993 | Becher | |
| 5,240,914 A | 8/1993 | Rubin | |
| 5,270,358 A | 12/1993 | Asmus | |
| 5,275,827 A | 1/1994 | Spinelli et al. | |
| 5,312,335 A | 5/1994 | McKinnon et al. | |
| D349,958 S | 8/1994 | Hollis et al. | |
| 5,369,155 A | 11/1994 | Asmus | |
| 5,372,589 A | 12/1994 | Davis | |
| 5,383,851 A | 1/1995 | McKinnon, Jr. et al. | |

(Continued)

FOREIGN PATENT DOCUMENTS

CA 2242033 1/1999

(Continued)

OTHER PUBLICATIONS

Medline Abstract 86149894, available from STN on Mar. 1990.*

(Continued)

*Primary Examiner*—John Pak
(74) *Attorney, Agent, or Firm*—Fish & Richardson P.C.

(57) ABSTRACT

The invention relates to a method to induce apoptosis and to inhibit matrix metalloproteinases in a disease condition in a human or animal by contacting hyperplastic tissue, tumor tissue, or a cancerous lesion with one or more antimicrobial metals, preferably formed with atomic disorder, and preferably in a nanocrystalline form. In another aspect of the invention, there is provided a method of preventing excessive release of matrix metalloproteinases from an inflammatory cell in a disease condition in a human or an animal by contacting the cell with a therapeutically effective amount of a noble metal in a crystalline form characterized by atomic disorder, or with a solution derived therefrom to provide a modulatory effect on one or more matrix metalloproteinases, wherein the one or more noble metals is formed with atomic disorder, and preferably in a nanocrystalline form. The nanocrystalline antimicrobial or noble metal of choice may be used in the form of a nanocrystalline coating of one or more antimicrobial or noble metals, a nanocrystalline powder of one or more antimicrobial or noble metals, or a solution containing dissolved species from a nanocrystalline powder or coating of one or more antimicrobial or noble metals.

40 Claims, 6 Drawing Sheets

U.S. PATENT DOCUMENTS

| | | | |
|---|---|---|---|
| 5,399,163 A | 3/1995 | Peterson et al. | |
| 5,454,886 A | 10/1995 | Burrell et al. | |
| 5,454,889 A | 10/1995 | McNicol et al. | |
| 5,457,015 A | 10/1995 | Boston | |
| 5,520,639 A | 5/1996 | Peterson et al. | |
| 5,534,288 A | 7/1996 | Gruskin et al. | |
| 5,563,132 A | 10/1996 | Bodaness | 514/185 |
| 5,569,207 A | 10/1996 | Gisselberg et al. | |
| 5,578,073 A | 11/1996 | Haimovich et al. | |
| 5,631,066 A | 5/1997 | O'Brien | |
| 5,681,575 A | 10/1997 | Burrell et al. | |
| 5,744,151 A | 4/1998 | Capelli | |
| 5,753,251 A | 5/1998 | Burrell et al. | |
| 5,770,255 A | 6/1998 | Burrell et al. | 427/2.1 |
| 5,770,258 A | 6/1998 | Takizawa | |
| 5,792,793 A | 8/1998 | Oda et al. | |
| 5,837,275 A | 11/1998 | Burrell et al. | |
| 5,848,995 A | 12/1998 | Walder | |
| 5,895,419 A | 4/1999 | Tweden et al. | |
| 5,899,880 A | 5/1999 | Bellhouse et al. | |
| 5,945,032 A | 8/1999 | Breitenbach et al. | |
| 5,958,440 A | 9/1999 | Burrell et al. | |
| 5,981,822 A | 11/1999 | Addison | |
| 5,985,308 A | 11/1999 | Burrell et al. | |
| 6,010,478 A | 1/2000 | Bellhouse et al. | |
| 6,013,050 A | 1/2000 | Bellhouse et al. | |
| 6,017,553 A | 1/2000 | Burrell et al. | |
| 6,022,547 A | 2/2000 | Herb et al. | |
| 6,071,541 A | 6/2000 | Murad | |
| 6,071,543 A | 6/2000 | Thornfeldt | |
| 6,096,002 A | 8/2000 | Landau | |
| 6,123,925 A | 9/2000 | Barry et al. | |
| 6,126,931 A | 10/2000 | Sawan et al. | 424/78.09 |
| 6,165,440 A | 12/2000 | Esenaliev | 424/1.11 |
| 6,187,290 B1 | 2/2001 | Gilchrist et al. | |
| 6,197,351 B1 | 3/2001 | Neuwirth | |
| 6,201,164 B1 | 3/2001 | Wulff et al. | |
| 6,224,898 B1 | 5/2001 | Balogh et al. | 424/445 |
| 6,238,686 B1 | 5/2001 | Burrell et al. | |
| 6,258,385 B1 | 7/2001 | Antelman | |
| 6,277,169 B1 | 8/2001 | Hampden-Smith et al. | |
| 6,294,186 B1 | 9/2001 | Beerse et al. | |
| 6,333,093 B1 | 12/2001 | Burrell et al. | |
| 6,365,130 B1 | 4/2002 | Barry et al. | |
| 6,720,006 B1 | 4/2004 | Hanke et al. | |
| 2001/0010016 A1 | 7/2001 | Modak et al. | |
| 2002/0001628 A1 | 1/2002 | Ito | |
| 2002/0016585 A1 | 2/2002 | Sachse | |
| 2002/0025344 A1 | 2/2002 | Newman et al. | 424/618 |
| 2002/0045049 A1 | 4/2002 | Madsen | |
| 2002/0051824 A1 | 5/2002 | Burrell et al. | |
| 2002/0192298 A1 | 12/2002 | Burrell et al. | |
| 2004/0009964 A1* | 1/2004 | Capelli | 514/184 |

FOREIGN PATENT DOCUMENTS

| | | |
|---|---|---|
| CN | 1082645 | 2/1994 |
| CN | 1241662 | 1/2000 |
| CN | 1279222 | 1/2001 |
| CN | 1291666 | 4/2001 |
| CN | 1291667 | 4/2001 |
| CN | 1306117 | 8/2001 |
| CN | 1322474 | 11/2001 |
| CN | 1322874 | 11/2001 |
| CN | 1328819 | 1/2002 |
| CN | 1328827 | 1/2002 |
| DE | 2748882 | 5/1979 |
| DE | 3807944 | 9/1989 |
| DE | 195 41 735 A1 | 5/1997 |
| EP | 0 136 768 | 4/1985 |
| EP | 0 254 413 | 1/1988 |
| EP | 0 356 060 | 8/1989 |
| EP | 0 355 009 | 2/1990 |
| EP | 0 378 147 | 7/1990 |
| EP | 0 599 188 | 6/1994 |
| EP | 0 681 841 A1 | 11/1995 |
| EP | 0681841 | 11/1995 |
| EP | 0780138 | 6/1997 |
| EP | 0 328 421 A2 | 8/1999 |
| EP | 1 159 972 | 12/2001 |
| GB | 420052 | 11/1934 |
| GB | 427106 | 4/1935 |
| GB | 965010 | 7/1964 |
| GB | 1270410 | 4/1972 |
| GB | 2 073 024 | 10/1981 |
| GB | 2 140 684 | 12/1984 |
| HU | 980078 A | 9/1999 |
| IT | 022309 | 12/1990 |
| JP | 60-21912 | 2/1985 |
| JP | SHO 58-126910 | 2/1985 |
| JP | 04244029 A | 9/1992 |
| JP | 11 060493 A | 3/1999 |
| JP | 11060493 | 3/1999 |
| JP | 11 116488 | 4/1999 |
| JP | 11116488 | 4/1999 |
| JP | H11-116488 | 4/1999 |
| JP | 11 124335 | 5/1999 |
| JP | 11124335 | 5/1999 |
| JP | H11-124335 | 5/1999 |
| JP | 2000 327578 | 11/2000 |
| JP | 2000327578 | 11/2000 |
| WO | 87/07251 | 12/1987 |
| WO | WO 89/09054 | 10/1989 |
| WO | 92/13491 | 8/1992 |
| WO | 93/23092 | 11/1993 |
| WO | WO 93/23092 | 11/1993 |
| WO | 95/13704 | 5/1995 |
| WO | WO 95/13704 | 5/1995 |
| WO | WO 96/17595 | 6/1996 |
| WO | 98/41095 | 9/1998 |
| WO | WO 98/41095 | 9/1998 |
| WO | 98/51273 | 11/1998 |
| WO | 00/27390 | 5/2000 |
| WO | WO 00/27390 | 5/2000 |
| WO | 00/30697 | 6/2000 |
| WO | 00/44414 | 8/2000 |
| WO | 00/64505 | 11/2000 |
| WO | 00/64506 | 11/2000 |
| WO | WO 00/78281 | 12/2000 |
| WO | WO 00/78282 | 12/2000 |
| WO | 01/15710 | 3/2001 |
| WO | 01/24839 | 4/2001 |
| WO | 01/27365 | 4/2001 |
| WO | WO 01/26627 | 4/2001 |
| WO | 01/34686 | 5/2001 |
| WO | 01/41774 | 6/2001 |
| WO | 01/41819 | 6/2001 |
| WO | 01/43788 | 6/2001 |
| WO | 01/49115 | 7/2001 |
| WO | 01/49301 | 7/2001 |
| WO | WO 01/49301 | 7/2001 |
| WO | WO 01/49302 | 7/2001 |
| WO | WO 01/49303 | 7/2001 |
| WO | 01/68179 A1 | 9/2001 |
| WO | 01/70052 | 9/2001 |
| WO | WO 01/74300 | 10/2001 |
| WO | 01/80920 | 11/2001 |
| WO | 02/09729 | 2/2002 |
| WO | 02/15698 | 2/2002 |
| WO | 02/18003 | 3/2002 |
| WO | WO 02/18699 | 3/2002 |
| WO | 02/44625 | 6/2002 |
| WO | WO 02/09729 A2 | 8/2002 |
| WO | 02/085299 A2 | 10/2002 |
| WO | 02/085384 A2 | 10/2002 |

| | | | |
|---|---|---|---|
| WO | 02/085385 A2 | 10/2002 | |
| WO | 02/085386 A2 | 10/2002 | |
| WO | 02/085387 A2 | 10/2002 | |

OTHER PUBLICATIONS

Derwent Abstract, Accession No. 2000-585653, abstracting RU 2146127 (Mar. 2000).*

Hoet, Peter H.M. et al., "Nanoparticles—known and unknown health risks," Journal of Nanobiotechnology, 2004, vol. 2, pp. 1-15.*

Borm, Paul J.A. et al., "Toxicological hazards of inhaled nanoparticles—potential implications for drug delivery, " Journal of Nanoscience and Nanotechnology, 2004, vol. 4(5), pp. 521-531.*

Ozkan, M., "Quantum dots and other nanoparticles: what can they offer to drug discovery?" Drug Discovery Today, 2004, vol. 9(24), pp. 1065-1071.*

Williams, D., "Nanocrystalline metals: another opportunity for medical devices?" Medical Device Technology, 2003, vol. 14(9), p. 12 (pp. 1-4 in the copy obtained via ProQuest).*

Grier, N., "Silver and its compounds," in: Block, S.S. Disinfection, Sterilization and Preservation, Lea & Febiger, Philadelphia, pp. 396-407, 1977.*

Merle E. Olson et al "Healing of Porcine Donor Sites Covered with Silver-Coated Dressing", Eur J Surg 2000; 166: 486-489.

Burrell, et al. "Efficacy of Silver-Coated Dressing as Bacterial Barriers in a Rodent Burn Sepsis Model" *Wounds* 1999; 11(4): 64-71.

Demling, et al., "The Role of Silver in Wound Healing: Effects of Silver on Wound Management," *Wounds*, vol. 13, No. 1, Jan./Feb. 2001 Supplement A; pp. 5-14.

Djokic et al., "An Electrochemical Analysis of Thin Silver Films Produced by Reactive Sputtering", *Journal of the Electrochemical Society*, 148 (3) C191-C196 (2001).

Kirsner, et al., "The Role of Silver in Wound Healing: Matrix Metalloproteinases in Normal and Impaired Wound Healing: A Potential Role of Nanocrystalline Silver," *Wounds*, vol. 13, No. 3, May/Jun. 2001, Supplement C pp. 5-12.

Ovington, "The Role of Silver in Wound Healing: Why is Nanocrystalline Silver Superior? Nanocrystalline Silver: Where the Old and Familiar Meets a New Frontier," *Wounds*, vol. 13, No. 2, Mar./Apr. 2001, Supplement B; pp. 5-10.

Pages from www.burnsurgery.org, 2002.

Pages from www.burnsurgery.org, 2000.

Pages from www.nanocrystallinesilver.org, 2002.

Sant et al., "Novel duplex antimicrobial silver films deposited by magnetron sputtering", *Philosophical Magazine Letters*, 2000, vol. 80, No. 4, 249-256.

Tredget , "Evaluation of Wound Healing using Silver Dressing", Feb. 22, 1996.

Tredget et al., "A Matched-Pair, Randomized Study Evaluating the Efficacy and Safety of Acticoat* Silver-Coated Dressing for the Treatment of Burn Wounds," *Journal of Burn Care & Rehabilitation* Nov./Dec. 1998; 19:531-7.

Voigt, et al., "The Use of Acticoat as Silver Impregnated Telfa Dressings in a Regional Burn and Wound Care Center: The Clinicians View, " *Wounds*, vol. 13, No. 2, Mar./Apr. 2001, Supplement B; pp. 11-20.

Wright et al., "Early healing events in a procine model of contaminated wounds: effects of nanocrystalline silver on matrix metalloproteinases, cell apoptosis, and healing" *Wound Repair and Regeneration 2002*; 10:141-151.

Wright, et al., "The Comparative Efficacy of Two Antimicrobial Barrier Dressings: In-vitro Examination of Two Controlled Realease of Silver Dressings" *Wounds* vol. 10, No. 6 Nov./Dec. 1998, pp. 179-188.

Wright, et al., "Efficacy of Topical silver against fungal burn wound pathogens", *AJIC* vol. 27, No. 4, Aug. 1999.

Wright, et al., "Wound Management in an era of increasing bacterial antibiotic resistance: A role for topical silver treatment," *AJIC* vol. 26, No. 6; pp. 572-577 Dec. 1998.

Yin et al., "Comparative Evaluation of the Antimicrobial Activity of ACTICOAT* Antimicrobial Barrier Dressing" *Journal of Burn Care & Rehabilitation*, vol. 20, No. 3 May/Jun. 1999.

Yin, et al., "Effect of Acticoat Antimicrobial Barrier Dressing on Wound Healing and Graft Take", *Burn Care & Rehabilitation*, part 2 Jan./Feb. 1999.

Shigemasa et al., "Applications of Chitin and Chitosan for Biomaterials" *Biotechnology & Genetic Engineering Reviews* vol. 13 (14) pp. 383-420.

Thornton, "Deposition Technologies for Films and Coatings: Coating Deposition by Sputtering" *Materials Science Series 5* pp. 170-243 1982.

Thornton, "Influence of apparatus geometry and deposition conditions on the structure and topography of thick sputtered coatings" *J. Vac. Sci. Technol.*, vol. 11, No. 4, Jul./Aug. 1974.

Sant et al., "Morphology of Novel Antimicrobial Silver Films Deposited By Magnetron Sputtering" *Scripta Materiala*, vol. 41, No. 12, pp. 1333-1339, Nov. 19, 1999.

Kuwano, Kazuyoshi et al. "Signal Transduction Pathways of Apoptosis and Inflammation Induced by the Tumor Necrosis Factor Receptor Family." *Am. J. Respir. Cell Mol. Biol.*, 2000: 22, pp. 147-1490.

Ashkenazi, Avi et al. Apoptosis control by death and decoy receptors. *Cur. Opin. Cell Biol.* 1999:11, pp 255-260.

Jakupec, Michael et al. "Gallium and Other Group Metal Compounds as Antitumor Agents." *Met. Ions Bio. Syst.* 2004:42, pp 425-462.

WPIDS abstract 1966-11488F (1966).

WPIDS abstract 1989-312257 (1989).

Medline abstract, accession No. 96064219 (1996).

* cited by examiner

METHOD OF INDUCTION OF APOPTOSIS AND INHIBITION OF MATRIX METALLOPROTEINASES USING ANTIMICROBIAL METALS

CROSS REFERENCE TO RELATED APPLICATIONS

This application is a continuation-in-part and claims the benefit of priority under 35 U.S.C. §120 of: U.S. patent application Ser. No. 09/840,637, filed Apr. 23, 2001, and entitled "Treatment of Acne;" U.S. Provisional Patent Application Ser. No. 60/285,884, filed Apr. 23, 2001, and entitled "Therapeutic Treatments Using the Direct Application of Noble Metal Compositions;" U.S. patent application Ser. No. 10/128,208, filed Apr. 23, 2002, and entitled "Therapeutic Treatments Using the Direct Application of Noble Metal Compositions;" U.S. patent application Ser. No. 10/131,509, filed Apr. 23, 2002, and entitled "Treatment of Mucosal Membranes;" U.S. patent application Ser. No. 10/131,511, filed April 23, 2002, and entitled "Treatment of Inflammatory Skin Conditions;" U.S. patent application Ser. No. 10/131,568, filed Apr. 23, 2002, and entitled "Method of Induction of Apoptosis and Inhibition of Matrix Metalloproteinases Using Antimicrobial Metals. Each of these applications is incorporated by reference herein.

FIELD OF THE INVENTION

The present invention relates to methods to induce apoptosis and to inhibit matrix metalloproteinases in a disease condition in a human or animal by contacting hyperplastic tissue, tumor tissue, or a cancerous lesion, and methods to modulate matrix metalloproteinases in an inflammatory cell in a human or animal; methods for the preparation of pharmaceutical compositions; and uses thereof.

BACKGROUND OF THE INVENTION

Apoptosis and matrix metalloproteinases (MMPs) have been implicated in many pathological diseases, such as cancer. Apoptosis or programmed cell death is a system which removes unnecessary, aged, or damaged cells. Apoptosis occurs during development to ensure proper formation of the fingers and toes in the fetus and of synapses between neurons in the brain; and serves to eradicate virus-infected cells, unnecessary immune cells, cells with DNA damage, and cancer cells. Decreased apoptosis has been implicated in developmental malformation, cancer and autoimmune disease, while enhanced apoptosis has been associated with degenerative diseases such as Alzheimer's disease, AIDS dementia, and Huntington's disease.

Caspases are a family of proteases, including initiator (activator) and effector (executioner) protease types, which regulate proteolysis during apoptosis. Apoptosis is triggered by signals which are either internal or external to the cell. In a healthy cell, the protein Bcl-2 is expressed on the surface and is bound to the protein Apaf-1. Internal damage in the cell causes Bcl-2 to release Apaf-1 and to no longer keep cytochrome c from leaking out of the mitochondria. The released cytochrome c and Apaf-1 bind to molecules of caspase 9. The resulting complex of cytochrome c, Apaf-1, caspase 9, and ATP aggregates in the cytosol. In cleaving a protein, caspase 9 activates other caspases, leading to digestion of structural proteins in the cytoplasm, degradation of chromosomal DNA, and phagocytosis of the cell. With regard to external signals (e.g., as in cytotoxic T cells inducing apoptosis in a virus-infected cell), binding of a death activator (FasL and Tumor necrosis factor or TNF) to the Fas and TNF receptor proteins on the surface of a target cell activates caspase 8, which activates other caspases leading to phagocytosis of the target cell.

Cancer cells may have mechanisms to avoid apoptosis. For example, some B-cell leukemias and lymphomas express high levels of Bcl-2, thus blocking apoptotic signals they may receive. Melanoma cells avoid apoptosis by inhibiting the expression of the gene which encodes Apaf-1. Lung and colon cancer cells secrete a molecule which binds to FasL, inhibiting its binding to Fas. Currently, radiation and standard chemotherapeutic drugs are used to induce apoptosis in some types of cancer cells; however, with such treatments having undesirable side effects and some cancers being resistant to such therapies, there exists a need to provide an effective approach which lacks such side effects, and demonstrates minimal interference with normal cell function.

Cancer tissue may also be treated with inhibitors of MMPs. Excessive MMPs have been implicated with diseases associated with the excessive degradation of extracellular matrix, such as tumor invasion and metastasis, arthritic diseases (rheumatoid arthritis and osteoarthritis), bone resorptive diseases (such as osteoporosis), enhanced collagen destruction associated with diabetes, periodontal disease, corneal ulceration, and ulceration of the skin.

MMPs are a family of at least 20 enzymes (proteases), including collagenases, gelatinases, stromelysins and stromelysin-like proteases as follows:

i) Collagenases include MMP-1 (interstitial), MMP-8 (neutrophil), and MMP-13, which catalyze the initial degradation of native collagen types I, II, III and VII. Collagen is an essential component of the extracellular matrix of tissues such as cartilage, bone, tendon and skin. MMP-13 is associated with osteoarthritis, ulcers and malignant tumor invasion.

ii) Gelatinases include MMP-2 (secreted by fibroblasts and a wide variety of other cell types) and MMP-9 (released by mononuclear phagocytes, neutrophils, corneal epithelial cells, tumor cells, cytotrophoblasts and keratinocytes). The gelatinases degrade gelatins (denatured collagens) and collagen type IV (basement membrane).

iii) Stromelysins include MMP-3, MMP-10 and MMP-11. MMP-3 and MMP-10 are expressed by epithelial cells and carcinomas, and degrade a broad range of extracellular matrix substrates, including laminin, fibronectin, proteoglycans, and collagen types IV and IX. MMP-11 is expressed by fibroblasts, and cleaves serine protease inhibitors.

iv) Stromelysin-like MMPs include MMP-12 and MMP-7. MMP-12 is expressed by macrophages and stromal cells, and degrades elastin. MMP-7 or matrilysin is expressed by mononuclear phagocytes and sporadically in tumors, and degrades a wide range of matrix substrates including proteoglycans, gelatins, fibronectin, elastin, and laminin.

MMPs are involved in the degradation of connective tissues, such as collagen, elastins, fibronectin, laminin, and other components of the extracellular matrix. Such components are present in the linings of joints, interstitial connective tissues, basement membranes, and cartilage. MMPs are present in various cell types which reside in or are associated with connective tissue, such as fibroblasts, monocytes, macrophages, endothelial cells, and invasive or metastatic tumor cells. Expression of MMPs may be induced by a variety of factors, including growth factors, chemical agents, physical stress, cell-matrix interactions, cell-cell interactions, oncogenic transformation, and cytokines. Cytokines affect the magnitude of inflammatory or immune responses, and can be divided into several groups, which include interferons, tumor necrosis factor (TNF), interleukins (IL-1 to IL-8), transforming growth factors, and the hematopoietic colony-stimulating factors.

MMPs and cytokines are associated and interact in various ways. Macrophages produce MMPs and also amplify inflammation by secreting cytokines, such as TNF-α and IL-1β. TNF-α promotes maturation of macrophages and neutrophils, while IL-1β promotes T and B cell proliferation and activation, and proteolysis. Cytokines, such as TNF-α and IL-1β, can regulate the transcription of MMPs, or lead to increased processing of MMPs from inactive to active forms. MMPs can also affect cytokines by inducing the release of membrane-bound cytokines, resulting in inhibition or activation of the cytokine depending on the particular type; using cytokines as substrates for MMP activity; and cleaving cytokines, such as TNF, from inactive to active forms. Inhibitors of MMPs may serve as potential therapeutic agents. A variety of naturally occurring or synthetic MMP inhibitors have been developed, including secondary amines (EP 159,396 to Searle); hydroxamic acid derivatives (EP 498,665 to Beckett et al.); collagenase inhibitors (EP 497,192 to Lobb et al.; U.S. Pat. No. 4,918,105 to Cartwright et al.); synthetic inhibitors (U.S. Pat. No. 5,773,438 to Levy et al.); tetracycline compounds (U.S. patent application Publication No. 2002/0045603 A1 to Golub et al.) and others known in the art. However, certain hydroxamic acids and derivatives thereof which have been suggested as collagenase inhibitors appear to be potentially toxic due to the hydroxamic moeity. Undesirable side effects specifically associated with use of MMP inhibitors have been reported, such as joint pain and exacerbation of liver injury (U.S. patent application Publication No. 2002/0035065 A1 to Bird et al.).

Modulation rather than total inhibition of MMPs and cytokines is desired for some conditions such as wound healing, where MMPs are required for angiogenesis and cell migration. Prolonged inflammatory response in a wound can delay healing, resulting in the destruction of tissue by processes which normally promote healing and synthesis of new tissue. MMPs are normally present in wounds for the purpose of breaking down damaged tissue in a controlled manner. However, elevated MMP activity impairs healing by degrading new tissue and growth factors, thereby damaging viable cells and the wound surface. There thus exists a need for a non-toxic, effective treatment to inhibit or modulate MMPs depending upon the disease of interest.

A treatment which provides a two-fold approach, namely induction of apoptosis of particular cells and inhibition of MMPs to eradicate cancer cells, and to reduce tissue damage contributing to tumor invasion and metastasis, may be desirable. Currently, cis-platin and its variations have been used as pro-apoptotic, anti-cancer agents, since the platinum complex attacks the DNA of tumor cells, thus disrupting RNA synthesis. However, cis-platin can pass through the blood to the kidneys and be immediately excreted; bind to proteins and be rendered inactive before reaching the tumor cells; or attack cells which are not tumors. Since acute toxicity may occur with long term use, cis-platin is restricted to short term, high doses. Sustained release to maintain treatment efficacy and non-toxicity in an anti-tumor agent are desirable.

Further, there are diseases and conditions for which MMP activity requires modulation, rather than total inhibition, to restore normal MMP activity. Although onset of inflammation is required for wound healing for example, excessive release, hence activity, of inflammatory mediators such as MMPs and cytokines contribute to wound damage, thus delaying healing.

While the patent literature reports that silver metal or silver salts such as silver nitrate, silver halides or silver sulphadiazine are among useful antibacterial agents, they have not, to the inventors' knowledge, been known or adopted to induce apoptosis and/or inhibit or modulate MMPs. For tumor tissue and cancerous lesions, there may be benefits associated with enhanced cellular apoptosis and inhibition of MMPs; for example, induction of apoptosis may aid in tumor suppression by eradicating tumor cells and by reducing the chance of tumor invasion and metastasis through inhibition of MMPs. In addition to affecting cancer cells, such treatment may be beneficial in eradicating excessive, normal cells, as in hyperplastic tissue in which abnormal multiplication or increase in the number of cells in a normal arrangement in normal tissue or an organ has occurred. In other diseases or a wound for example, modulation of MMPs rather than total inhibition may be desired.

SUMMARY OF THE INVENTION

The inventors have established that antimicrobial metals formed with atomic disorder and preferably in a nanocrystalline form, induce apoptosis and inhibit MMPs. Treatment of hyperplastic tissue, tumor tissue, or cancerous lesions with antimicrobial metals having pro-apoptotic and anti-MMP effects is thereby indicated.

Further, treatment of wounds or diseases with antimicrobial metals having modulating effects on MMPs is indicated. Through an animal model (Example 4) and a clinical study (Example 5), taken together with the evidence that the silver materials herein disclosed are capable of reducing inflammation (see co-pending U.S. patent application Ser. No. 10/131,568, filed on Apr. 23, 2002; Ser. No. 10/131,511, filed on Apr. 23, 2002; Ser. No. 10/131,509, filed on Apr. 23, 2002; Ser. No. 10/131,513, filed on Apr. 23, 2002, which is now U.S. Pat. No. 6,723,350; and co-pending U.S. patent application Ser. No. 09/840,637 filed Apr. 23, 2001, and U.S. Provisional Patent Application No. 60/285,884 filed Apr. 23, 2001), the inventors have demonstrated a method of reducing inflammation in a patient in need thereof, by contacting an area of inflammation with nanocrystalline silver characterized by sufficient atomic disorder, in a therapeutically effective amount sufficient to modulate the production of one or both of MMP-9 and TNF-α.

Conditions characterized by undesirable MMP activity include ulcers, asthma, acute respiratory distress syndrome, skin disorders, skin aging, keratoconus, restenosis, osteo- and rheumatoid arthritis, degenerative joint disease, bone disease, wounds, cancer including cell proliferation, invasiveness, metastasis (carcinoma, fibrosarcoma, osteosarcoma), hypovolemic shock, periodontal disease, epidermolysis bullosa, scleritis, atherosclerosis, multiple sclerosis, inflammatory diseases of the central nervous system, vascular leakage syndrome, collagenase induced disease, adhesions of the peritoneum, strictures of the esophagus or bowel, ureteral or urethral strictures, and biliary strictures. Excessive TNF production has been reported in diseases which are characterized by excessive MMP activity, such as autoimmune disease, cancer, cachexia, HIV infection, and cardiovascular conditions.

The present application demonstrates that modulation of the levels of active MMPs (hence, MMP activity) and cytokines such as TNF-α to promote wound healing can be mediated by nanocrystalline silver ions characterized by atomic disorder. When delivered to a wound surface, such ions appear to modulate the levels of active MMPs and cytokines, notably TNF-α. Such modulation appears to assist in controlling the proteolytic environment of the wound, thereby promoting healing.

This new treatment thus has the dual advantages of being both pro-apoptotic and an inhibitor or modulator of MMPs depending upon the disease or condition of interest. Methods and formulations of this invention have application to both humans and animals.

The antimicrobial metals selected from one or more of silver, gold, platinum and palladium, are formed with atomic disorder, such that ions, clusters, atoms or molecules of the metals are released at a concentration sufficient to provide localized pro-apoptotic and anti-MMP effects. Most preferably, the antimicrobial metals are in a nanocrystalline form, and include sufficient atomic disorder to provide such effects on a sustainable basis.

Without being bound by the same, it is believed that the nanocrystalline antimicrobial metals formed with atomic disorder are capable of releasing highly active clusters of the antimicrobial metal (example clusters of $Ag^0$ or $Ag^+/Ag^0$), which are responsible for the surprisingly enhanced antimicrobial activity and the surprising presence of the anti-inflammatory activity in the treatment of mucosal membranes, compared with other known antimicrobials such as silver salts (ex. silver nitrate), silver zeolites which release only $Ag^+$, or silver metal and silver oxide which have only minor solubility. Clusters are known to be small groups of atoms, ions or the like, as described by R. P. Andres et al., "Research Opportunities on Cluster and Cluster-Assembled Materials", J. Mater. Res. Vol 4, No 3, 1989, p. 704. For silver, clusters are believed to contain less than the 14 atoms of a normal face centered cubic crystal lattice form of silver.

The crystalline forms of these antimicrobial metals may be used in, or formulated from, any of the following formats:
i) coatings of the antimicrobial metals on medical grade substrates, for example, dressings, packings, meshes, films, filtering surfaces, filters, infusers, fibres, containers or vials, from materials composed of for example polyethylene, high density polyethylene, polyvinylchloride, latex, silicone, cotton, rayon, polyester, nylon, cellulose, acetate, carboxymethylcellulose, alginate, chitin, chitosan and hydrofibres;
ii) powders, preferably prepared as nanocrystalline powders of the antimicrobial metals, or as nanocrystalline coatings of the antimicrobial metals on biocompatible substrates in powder form, preferably on bioabsorbable and/or hygroscopic substrates such as:
  Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers, or
  Naturally Derived Polymers: Proteins: albumin, fibrin, collagen, elastin; Polysaccharides: chitosan, alginates, hyaluronic acid; and
  Biosynthetic Polyesters: 3-hydroxybutyrate polymers;
iii) occlusions or hydrated dressings, in which the dressing is impregnated with a powder or solution of the antimicrobial metals, or is used with a topical formulation of the antimicrobial metals, with such dressings for example as hydrocolloids, hydrogels, polyethylene, polyurethane, polyvinylidine, siloxane or silicone dressings;
iv) gels, formulated with nanocrystalline powders or solutions of the antimicrobial metals with such materials as carboxymethylcellulose, alginate, chitin, chitosan and hydrofibres, together with such ingredients as preservatives, pectin and viscosity enhancers;
v) creams, lotions, pastes and ointments formulated with nanocrystalline powders or solutions of the antimicrobial metals, for example as emulsions or with drying emollients; and
vi) liquids, formulated as solutions by dissolving nanocrystalline coatings or powders of the antimicrobial metals, for example as topical solutions, aerosols, mists, sprays, drops, infusions and instillation solutions for body cavities such as the bladder, prostate, lung, and liver.

Solutions of the antimicrobial metals lose some activity with aging and are thus either stabilized or generated fresh for administration. Alternatively, the antimicrobial metals may be packaged for convenient solution generation, for instance in a pervious membrane such as a tea bag type infuser. Other two part or two phase systems may be used in which the nanocrystalline metal is separated from the water or electrolyte solvent, for example in kit form, with the antimicrobial metal being provided in dissolving capsules, as a coating on the inside of vials or containers, on substrates such as dressing, separated by a membrane which can be perforated, or in a separate container from the carrier, in a tea bag-type infuser etc.

In the above formats, the nanocrystalline antimicrobial metals are formulated from nanocrystalline coatings or nanocrystalline powders of the nanocrystalline antimicrobial metals, or from solutions prepared by dissolving the nanocrystalline coatings or powders therein. The formulations include a therapeutically effective amount of the coatings or powders, and most preferably, the following amounts:

| | |
|---|---|
| For coatings: | 150–3000 nm thick coatings for substrates, or thicker for forming powders (such coatings can be used to generate 0.001 to 10% by weight solutions) |
| For gels, creams etc.: | 0.01–30% by weight, more preferably 0.01–10% by weight and most preferably 0.1–5% by weight of the antimicrobial or noble metal powder |
| For liquids: | 0.001–10% by weight, more preferably 0.01 to 5% by weight and most preferably 0.1 to 1% by weight of the antimicrobial or noble metal (generated from any format, including coatings, flakes, powders). |

Concentrations of the antimicrobial or noble metal species in solution will vary according to the application, formulation and subject, but will generally range from 1–5000 $\mu$g/ml, more preferably 20–3000 $\mu$g/ml, more preferably 40–800 $\mu$g/ml, and most preferably 50–500 $\mu$g/ml.

Nanocrystalline coatings of the antimicrobial metals are most preferably deposited onto substrates such as dressings, for example one or more layers of medical dressing materials which can be laminated with uncoated layers of medical dressing materials. The coatings can be prepared by known techniques for preparing nanocrystalline coatings, but are most preferably prepared by physical vapour deposition under conditions which create atomic disorder. The nanocrystalline coatings may be prepared to create an interference colour so as to provide an indicator, as described in prior patent application WO 98/41095, published Sep. 24, 1998, and naming inventors R. E. Burrell and R. J. Precht.

Nanocrystalline powders of the antimicrobial metals may be prepared as nanocrystalline coatings, preferably of the above thickness, on powdered substrates such as chitin, or may be prepared as nanocrystalline coatings on a substrate such as a silicon wafer, and then scraped off as a nanocrystalline powder. Alternatively, fine grained or nanocrystalline powders of the antimicrobial metals may be cold worked to impart atomic disorder, as taught in prior patent applications WO 93/23092, published Nov. 25, 1993, and WO 95/13704, published May 26, 1995, both of which name Burrell et al., as inventors.

Thus, the invention broadly provides a method of inducing apoptosis in a disease condition in a human or an animal, which comprises:

contacting a hyperplastic tissue, a tumor tissue, or a cancerous lesion with a therapeutically effective amount of the antimicrobial metals in a crystalline form to provide a localized pro-apoptotic effect, wherein the antimicrobial metals are characterized by sufficient atomic disorder, such that the metal, in contact with an alcohol or water-based electrolyte, releases atoms, ions, molecules, or clusters of at least one antimicrobial metal at a concentration sufficient to provide a localized pro-apoptotic effect. The antimicrobial metals further inhibit one or more matrix metalloproteinases or modulate the production of the one or more matrix metalloproteinases.

In another broad aspect of the invention, there is provided a method of preventing excessive release of one or more matrix metalloproteinases from an inflammatory cell in a disease condition in a human or an animal, which comprises:

contacting the cell with a therapeutically effective amount of a noble metal in a crystalline form characterized by atomic disorder, or with a solution derived therefrom, to provide a modulating effect on one or more matrix metalloproteinases, wherein the noble metal is formed with sufficient atomic disorder, such that the metal, in contact with an alcohol or water-based electrolyte, releases atoms, ions, molecules, or clusters of at least one noble metal at a concentration sufficient to provide a localized anti-MMP effect.

In another broad aspect of the invention, there is provided a method of reducing inflammation in patient in need thereof, which comprises:

contacting an area of inflammation with a therapeutically effective amount of a noble metal in a crystalline form characterized by disorder, or with a solution derived therefrom, to provide a modulating effect on one or more matrix metalloproteinases, wherein the noble metal is formed with sufficient atomic disorder, such that the metal, in contact with an alcohol or water-based electrolyte, releases atoms, ions, molecules, or clusters of at least one noble metal at a concentration sufficient to provide a localized anti-MMP effect.

As used herein and in the claims, the terms and phrases set out below have the meanings which follow.

"Apoptosis" means programmed cell death which removes unnecessary, aged, or damaged cells.

"Pro-apoptotic effect" means that atoms, ions, molecules or clusters of the antimicrobial or noble metal are released to contact a human or animal cell in a concentration sufficient to induce apoptosis.

"Inflammation" means a localized protective response elicited by injury or destruction of tissues, which serves to destroy, dilute, or sequester both the injurious agent and the injured tissue. It is characterized by pain, heat, redness, swelling, or loss of function.

"Anti-inflammatory effect" means a reduction in one or more of the symptoms of erythema (redness), edema (swelling), pain and pruritus.

"Anti-MMP effect" means that atoms, ions, molecules or clusters of the antimicrobial or noble metal are released to contact a human or animal cell in a concentration sufficient to inhibit one or more matrix metalloproteinases or modulate the production of one or more matrix metalloproteinases.

"Inhibition," "inhibit," "inhibiting," or "inhibitor" is meant to refer to the arrest or restraint of a process. An "inhibitor" means a substance which interferes with a chemical reaction, growth, or other biological activity, and acts to inhibit or hold in check the action of a tissue organizer.

"Modulation," "modulate," "modulating," or "modulator" is meant to refer to the act of tempering or toning down the release of one or more matrix metalloproteinases, or one or more cytokines. A "modulator" means a specific inductor which brings out characteristics peculiar to a definite region.

"Excessive release" means an amount which exacerbates or prolongs inflammation so as to prevent the condition from resolving.

"Matrix metalloproteinases" is meant to refer to any protease of the family of MMPs which are involved in the degradation of connective tissues, such as collagen, elastins, fibronectin, laminin, and other components of the extracellular matrix, and associated with conditions in which excessive degradation of extracellular matrix occurs, such as tumor invasion and metastasis.

"Gelatinases" is meant to refer to MMP-2 (secreted by fibroblasts and a wide variety of other cell types) and MMP-9 (released by mononuclear phagocytes, neutrophils, corneal epithelial cells, tumor cells, cytotrophoblasts and keratinocytes). The gelatinases degrade gelatins (denatured collagens) and collagen type IV (basement membrane).

"Cytokine" is meant to refer to a nonimmunoglobulin polypeptide secreted by monocytes and lymphocytes in response to interaction with a specific antigen, a nonspecific antigen, or a nonspecific soluble stimulus (e.g., endotoxin, other cytokines). Cytokines affect the magnitude of inflammatory or immune responses. Cytokines can be divided into several groups, which include interferons, tumor necrosis factor (TNF), interleukins (IL-1 to IL-8), transforming growth factors, and the hematopoietic colony-stimulating factors.

"Fibroblast" means a connective tissue cell which is a flat-elongated cell with cytoplasmic processes at each end having a flat, oval vesicular nucleus. Fibroblasts which differentiate into chondroblasts, collagenoblasts, and osteoblasts form the fibrous tissues in the body, tendons, aponeuroses, supporting and binding tissues of all sorts.

"Macrophage" means a highly phagocytic cell with a small, oval, sometimes indented nucleus and inconspicuous nucleoli, occurring in the walls of blood vessels and loose connective tissue. Macrophages are usually immobile, but become actively mobile when stimulated by inflammation.

"Neutrophil" means a granulocyte which arises from the bone marrow and is fully mature when it is released into the circulation. It functions in cellular defense primarily in phagocytosis.

"Polymorphonuclear leukocyte" is meant to refer to neutrophils. The name derives from the multiple lobes of the mature neutrophil's nucleus.

"Hyperplasia" means abnormal multiplication or increase in the number of cells in a normal arrangement in normal tissue or an organ.

"Tumor" means a spontaneous growth of tissue in which multiplication of cells is abnormal, uncontrolled and progressive. A tumor serves no useful function and grows at the expense of the healthy organism.

"Malignant" means a tumor which has the properties of anaplasia, invasion, and metastasis.

"Benign" means a tumor which is not malignant, recurrent, invasive, or progressive. A tumor or growth which is benign is noncancerous.

"Cancerous lesion" means a tumor of epithelial tissue, or malignant, new growth made up of epithelial cells tending to infiltrate surrounding tissues and to give rise to metastases. As used in reference to the skin, a cancerous lesion means a lesion which may be a result of a primary cancer, or a metastasis to the site from a local tumor or from a tumor in a distant site. It may take the form of a cavity, an open area on the surface of the skin, skin nodules, or a nodular growth extending from the surface of the skin.

"Metastasis" means the movement or spreading of cancer cells from one organ or tissue to another via the bloodstream, or lymph system.

"Autoimmune" disease is any group of disorders in which tissue injury is associated with humoral or cell-mediated responses to body constituents, for example, rheumatoid arthritis. They may be systemic or organ specific.

"Metal" or "metals" includes one or more metals whether in the form of substantially pure metals, alloys or compounds such as oxides, nitrides, borides, sulphides, halides or hydrides.

"Antimicrobial metals" are silver, gold, platinum, palladium, iridium, zinc, copper, tin, antimony, bismuth, or mixtures of these metals with same or other metals, silver, gold, platinum and palladium being preferred, and silver being most preferred.

"Noble metals" are silver, gold, platinum and palladium, or mixtures of such metals with same or other metals, with silver metal being the most preferred.

"Antimicrobial effect" means that atoms, ions, molecules or clusters of the antimicrobial or noble metal are released into the electrolyte which the coating contacts in concentration sufficient to inhibit microbial growth on and in the vicinity of the coating. The most common methods of measuring an antimicrobial effect are a zone of inhibition test (which indicates an inhibitory effect, whether microbiostatic or microbiocidal) or a logarithmic reduction test (which indicates a microbiocidal effect). In a zone of inhibition test (ZOI) the material to be tested is placed on a bacterial lawn (or a lawn of other microbial species) and incubated. A relatively small or no ZOI (ex. less than 1 mm) indicates a non-useful antimicrobial effect, while a larger ZOI (ex. greater than 5 mm) indicates a highly useful antimicrobial effect. The ZOI is generally reported as a corrected zone of inhibition (CZOI), wherein the size of the test sample is subtracted from the zone. A logarithmic reduction test in viable bacteria is a quantitative measure of the efficacy of an antibacterial treatment; for example, a 5 log reduction means a reduction in the number of microorganisms by 100,000-fold (e.g., if a product contained 100,000 pertinent microorganisms, a 5 log reduction would reduce the number of pertinent microorganisms to 1). Generally, a 3 log reduction represents a bactericidal effect. The logarithmic reduction test involves combining the inoculum with the test treatment, incubating the inoculum with the test treatment, recovering the bacteria or other microbial species, and enumerating the bacteria or other microbial species using serial dilutions. Examples of these tests are set out in the examples which follow.

"Biocompatible" means generating no significant undesirable host response for the intended utility. Most preferably, biocompatible materials are non-toxic for the intended utility. Thus, for human utility, biocompatible is most preferably non-toxic to humans or human tissues.

"Sustained release" or "sustainable basis" are used to define release of atoms, molecules, ions or clusters of an antimicrobial metal that continues over time measured in hours or days, and thus distinguishes release of such metal species from the bulk metal, which release such species at a rate and concentration which is too low to be therapeutically effective, and from highly soluble salts of antimicrobial metals such as silver nitrate, which releases silver ions virtually instantly, but not continuously, in contact with an alcohol or electrolyte.

"Atomic disorder" includes high concentrations one or more of: point defects in a crystal lattice, vacancies, line defects such as dislocations, interstitial atoms, amorphous regions, grain and sub grain boundaries and the like relative to its normal ordered crystalline state. Atomic disorder leads to irregularities in surface topography and inhomogeneities in the structure on a nanometer scale.

"Normal ordered crystalline state" means the crystallinity normally found in bulk metal materials, alloys or compounds formed as cast, wrought or plated metal products. Such materials contain only low concentrations of such atomic defects as vacancies, grain boundaries and dislocations.

"Diffusion", when used to describe conditions which limit diffusion in processes to create and retain atomic disorder, i.e. which freeze-in atomic disorder, means diffusion of atoms (adatom diffusion) and/or molecules on the surface or in the matrix of the material being formed.

"Alcohol or water-based electrolyte" is meant to include any alcohol or water-based electrolyte that the antimicrobial materials of the present invention might contact in order to activate (i.e. cause the release of species of the antimicrobial metal) into same. The term is meant to include alcohols (short chain ($C_6$ or less) and preferably $C_4$ or less), water, gels, fluids, solvents, and tissues containing, secreting, or exuding water or water-based electrolytes, including body fluids (for example blood, urine, or saliva), and body tissue (for example skin).

"Bioabsorbable" as used herein in association includes substrates which are useful in medical devices, that is which are biocompatible, and which are capable of bioabsorption in period of time ranging from hours to years, depending on the particular application.

"Bioabsorption" means the disappearance of materials from their initial application site in the body (human or mammalian) with or without degradation of the dispersed polymer molecules.

"Colour change" is meant to include changes of intensity of light under monochromatic light as well as changes of hue from white light containing more than one wavelength.

An "interference colour" is produced when light impinges on two or more partly reflective surfaces separated by a distance which bears the right relationship to the wavelength of the light to be removed by destructive interference.

"Partly reflective" when used to describe the base or top layer materials, means that the material has a surface which reflects a portion of incident light, but which also transmits a portion of the incident light. Reflection occurs when a ray of incoming light encounters a boundary or interface characterized by a change in refractive index between two media. For the top layer of the antimicrobial materials of this invention, that interface is with air. For the base layer, the interface is with the top layer. The reflectance of the base and top layers is balanced so as to generate an interference colour.

"Partly light transmissive" when used to describe a thin film of the top layer material means that the thin film is capable of transmitting at least a portion of incident visible light through the thin film.

"Detectable" when used to describe a colour change means an observable shift in the dominant wavelength of the reflected light, whether the change is detected by instrument, such as a spectrophotometer, or by the human eye. The dominant wavelength is the wavelength responsible for the colour being observed.

"Cold working" as used herein indicates that the material has been mechanically worked such as by milling, grinding, hammering, mortar and pestle or compressing, at temperatures lower than the recrystallization temperature of the material. This ensures that atomic disorder imparted through working is retained in the material.

"Pharmaceutically- or therapeutically-acceptable" is used herein to denote a substance which does not significantly interfere with the effectiveness or the biological activity of the active ingredients (pro-apoptotic and anti-MMP properties) and which has an acceptable toxic profile for the host to which it is administered.

"Therapeutically effective amount" is used herein to denote any amount of a formulation of the antimicrobial or noble metals which will exhibit either or both of a pro-apoptotic and anti-MMP effect, when applied to the affected area. A single application of the formulations of the present invention may be sufficient, or the formulations may be applied repeatedly over a period of time, such as several times a day for a period of days or weeks. The amount of the active ingredient, that is the antimicrobial or noble metal in the form of a coating, powder or dissolved in liquid solution, will vary with the conditions being treated, the stage of advancement of the condition, the age and type of host, and the type and concentration of the formulation being applied. Appropriate amounts in any given instance will be readily apparent to those skilled in the art or capable of determination by routine experimentation.

"Carrier" means a suitable vehicle including one or more solid, semisolid or liquid diluents, excipients or encapsulating substances which are suitable for administration to the area.

"Nanocrystalline" is used herein to denote single-phase or multi-phase polycrystals, the grain size of which is less than about 100, more preferably <50, even more preferably <40, even more preferably <30, and most preferably <25 nanometers in at least one dimension. The term, as applied to the crystallite or grain size in the crystal lattice of coatings, powders or flakes of the antimicrobial or noble metals, is not meant to restrict the particle size of the materials when used in a powder form.

"Powder" is used herein to include particulates of the antimicrobial or noble metals ranging from nanocrystalline (less than 100 nm) to submicron sized powders up to flakes. Preferably, powders of the antimicrobial or noble metals used in the present invention are sized at less than 100 $\mu$m, and more preferably less than 40 $\mu$m, and most preferably less than 10 $\mu$m.

"Grain size", or "crystallite size" means the size of the largest dimension of the crystals in the antimicrobial metal coating or powder.

"Hydrocolloid" means a synthetically prepared or naturally occurring polymer capable of forming a thickened gel in the presence of water and polyols (swelling agent). The swelling agent must be capable of swelling the hydrocolloid chosen in order to form the gel phase.

"Hydrogels" means a hydrocolloid swollen with water or another hydrophilic liquid which is used for absorbing or retaining moisture or water.

"Gel" means a composition that is of suitable viscosity for such purposes, e.g., a composition that is of a viscosity that enables it to be applied and remain on the skin.

When used herein and in the claims, the term "nanocrystalline antimicrobial metal" and similar terminology, such as "nanocrystalline coatings or powders" is meant to refer to antimicrobial metals formed with atomic disorder and having a nanocrystalline grain size.

DESCRIPTION OF THE PREFERRED EMBODIMENTS

Figure 1:
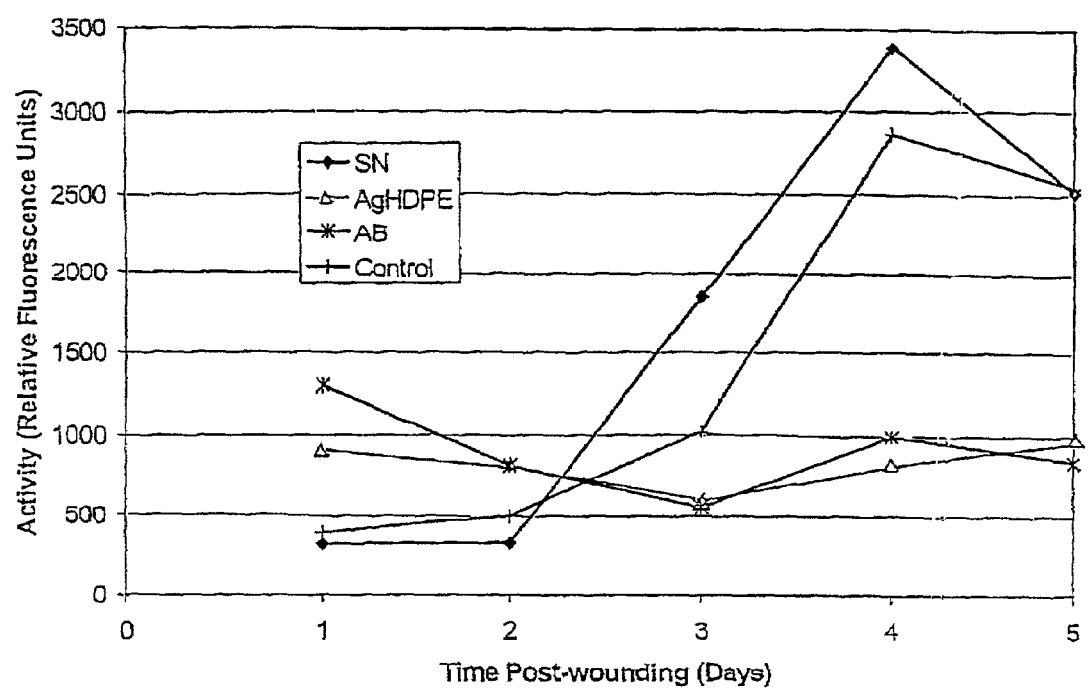
FIG. 1 is a graph showing MMP activity of incision fluids recovered from incisions dressed with silver-coated dressing (AB), silver nitrate moistened gauze (SN), silver-coated AgHDPE, and control dressing on each post-incision day.

Crystalline forms of the antimicrobial metals Ag, Au, Pt, and Pd can be prepared as coatings or powders, or as solutions prepared by dissolving the coatings or powders. The crystalline coatings or powders are most preferably formed with atomic disorder in accordance with the techniques published in the prior patent applications of Burrell et al., see for example WO 93/23092, published Nov. 25, 1993, WO 95/13704, published May 26, 1995 and WO 98/41095, published Sep. 24, 1998.

Pharmaceutical formulations for treatment of hyperplastic tissue, tumor tissue, cancerous lesions, and other diseases utilize the antimicrobial or noble metals in powder, coatings or solution form. Preparation of the antimicrobial or noble metals as powders or coatings is set out below in section A, format for formulations are set forth in section B, sterilization in section C, and formulating, dosages and treatment are set forth in section D.

A. Preparation of Crystalline Forms of the Antimicrobial Metals with Atomic Disorder a) Antimicrobial Metal Coatings on Dressings or Other Substrates Dressings or other substrates such as packings, vials, fabric, or fibres etc. may be coated with antimicrobial coatings formed with atomic disorder. The description below is directed to coatings on dressing materials, but the coating techniques are equally applicable to coating other substrates. Dressings coated with antimicrobial metals in accordance with the invention include one or more layers of medical dressing materials. Multiple layers may be laminated together by known means such as low temperature thermal fusing, stitching or, most preferably, ultrasonic welding.

The dressing may be formed to include an occlusive or semi-occlusive layer such as an adhesive tape or polyurethane film in order to secure the dressing in place, and retain moisture for release of ions, atoms, molecules or clusters of the antimicrobial metal (hereinafter antimicrobial metal species).

The preferred and alternate compositions of the dressing layers, together with the preferred nanocrystalline antimicrobial metal coatings, are set out in further detail below.

i) Dressing Materials

The dressing is formed of a perforated, preferably non-adherent material which allows for fluids to penetrate or diffuse there through in either or both directions. The perforated material may be formed of a woven or non-woven, non-woven being preferred, fabric such as cotton, gauze, a polymeric net or mesh such as polyethylene, nylon, polypropylene or polyester, an elastomer such as polyurethane or polybutadiene elastomers, or a foam such as open cell polyurethane foam. Exemplary perforated, non-adherent materials useful for the dressing include non-woven meshes such as DELNET™ P530, which is a non-woven veil formed of high density polyethylene using extrusion, embossing and orientation processes, produced by Applied Extrusion Technologies, Inc. of Middletown, Del., USA. This same product is available as Exu-Dry CONFORMANT 2™ Wound Veil, from Frass Survival Systems, Inc., Bronx, N.Y., USA as a subset of that company's Wound Dressing Roll (Non-Adherent) products. Other useful non-woven meshes include CARELLE™ or NYLON 90™, available from Carolina Formed Fabrics Corp., N-TERFACE™, available from Winfield Laboratories, Inc., of Richardson, Tex., USA. Exemplary woven meshes may be formed from fibreglass or acetate, or cotton gauze. An exemplary hydrophilic polyurethane foam is HYPOL™, available from W. R. Grace & Co., New York, N.Y., USA.

For ease of ultrasonic welding for lamination, at least one dressing layer is preferably formed from a polymeric material which is amenable to ultrasonic welding, that is which will melt on the application of localized heat and then fuse multiple layers together on cooling.

If desired, a second, absorbent layer is formed from an absorbent material for holding sufficient moisture next to the affected area in order to activate the antimicrobial metal coating, that is to cause release of ions, molecules, atoms or clusters of the antimicrobial metal in order to cause pro-apoptotic and anti-MMP effects. Preferably, the absorbent material is an absorbent needle punched non-woven rayon/polyester core such as SONTARA™ 8411, a 70/30 rayon/polyester blend commercially available from Dupont Canada, Mississauga, Ontario, Canada. This product is sold by National Patent Medical as an American White Cross sterile gauze pad. However, other suitable absorbent materials include woven or non-woven materials, non-woven being preferred made from fibers such as rayon, polyester, rayon/polyester, polyester/cotton, cotton and cellulosic fibers. Exemplary are creped cellulose wadding, an air felt of air laid pulp fibers, cotton, gauze, and other well known absorbent materials suitable for medical dressings.

A third layer of the dressing, if used, is preferably formed of perforated, non-adherent material such as used in the first layer. This allows moisture penetration as sterile water and the like are added in order to activate the antimicrobial metal coating.

Additional layers may be included between or above the first, second and third layers as is well known in medical dressings. The coated dressing layers may be combined with an adhesive layer, in a well known manner.

The dressing may be used as a single layer, or may be used as multiple layers laminated together at intermittent spaced locations across the dressing by ultrasonic welds. Ultrasonic welding is a known technique in the quilting art. Briefly, heat (generated ultrasonically) and pressure are applied to either side of the dressing at localized spots through an ultrasonic horn so as to cause flowing of at least one of the plastic materials in the first and second layers and the subsequent bonding together of the layers on cooling. The welds appear at localized circular spots and are preferably less than 0.5 cm in diameter.

The use of ultrasonic welding of the layers at spaced locations has the advantage of retaining the absorbent and moisture penetration properties of the dressing layers, while retaining the conforming properties of the dressing. Edge seams, stitching and adhesives have the disadvantage of interfering with one or more of these desirable properties of the dressings. Furthermore, by spacing the welds at intermittent locations across the dressing, the dressing may be cut to smaller sizes, as needed, without causing delamination. Preferred spacings of about 2.5 cm between welds allows the dressing to be cut down to about 2.5 cm sizes, while maintaining at least one weld to hold the laminated layers together.

ii) Nanocrystalline Coatings of Antimicrobial Metals

The coated substrate, for example a dressing, preferably includes a nanocrystalline coating of one or more of the antimicrobial metals. The coating is applied to one or more of the dressing layers, but is most preferably applied at least to the skin facing layer.

The nanocrystalline coating is most preferably formed with atomic disorder in accordance with the procedures set out above and as described in WO 93/23092, WO 95/13704, and WO98/41095, and as set out below. Most preferably, the coating is formed as a multilayer coating of the antimicrobial metals, having a top and a base layer, as set below, to produce an interference colour. In this way, the coating provides not only the active ingredient for treatment of hyperplastic tissue, tumor tissue, cancerous lesion, or other disease, but also acts as an indicator of activation of the dressing. As the top layer of the coating is activated with an alcohol or water-based electrolyte, such as sterile water or ethanol, even minor dissolution of the antimicrobial metal results in a detectable colour change, indicating that the coating has been activated. If there is no colour change, additional moisture might be provided to the dressing by adding water, until a colour change is detected. Once activated, the dressing should be maintained in a moist condition, for example by the addition of sterile water, if necessary.

iii) Multilayer Nanocrystalline Coatings of Antimicrobial Metals with Interference Colour The coated substrates, for example dressings may include the antimicrobial metal coating formed with at least two metal layers, a base layer and a top layer over the base layer, so as to produce an interference colour, as set forth in WO 98/41095, the teachings of which are incorporated herewith by reference. The indicator colour can function as an indicator when contacted with a water or alcohol based electrolyte, since the coating will change colour. An exemplary multilayer nanocrystalline coating of silver with a blue interference colour is set forth in Example 1.

iv) Nanocrystalline Coatings of Antimicrobial Metals Containing Atomic Disorder

The coatings of the present invention are formed in a crystalline form from one or more antimicrobial metals with atomic disorder. The production of atomic disorder through physical vapour deposition techniques is described in WO 93/23092 and WO 95/13704, and as outlined below.

The antimicrobial metal is deposited as a thin metallic film on one or more surfaces of the dressing by vapour deposition techniques. Physical vapour techniques, which are well known in the art, all deposit the metal from the vapour, generally atom by atom, onto a substrate surface. The techniques include vacuum or arc evaporation, sputtering, magnetron sputtering and ion plating. The deposition is conducted in a manner to create atomic disorder in the coating as defined above. Various conditions responsible for producing atomic disorder are useful. These conditions are generally those which one has been taught to avoid in thin film deposition techniques, since the object of most thin film depositions is to create a defect free, smooth and dense film (see for example J. A. Thornton, "Influence of Apparatus Geometry and Deposition Conditions on the Structure and Topography of Thick Sputtered Coatings," J. Vac. Sci. Technol., 11(4), 666–670, 1974).

The preferred conditions which are used to create atomic disorder during the deposition process include:

a low substrate temperature, that is maintaining the surface to be coated at a temperature such that the ratio of the substrate temperature to the melting point of the metal (in degrees Kelvin) is less than about 0.5, more preferably less than about 0.35 and most preferably less than about 0.3; and optionally one or both of:

a higher than normal working gas pressure (or ambient pressure in depositions not using a working gas), i.e. for vacuum evaporation: e-beam or arc evaporation, greater than 0.001 Pa (0.01 mT), gas scattering evaporation (pressure plating) or reactive arc evaporation, greater than 2.67 Pa (20 mT); for sputtering: greater than 10 Pa (75 mT); for magnetron sputtering: greater than about 1.33 Pa (10 mT); and for ion plating: greater than about 26.67 Pa (200 mT); and maintaining the angle of incidence of the coating flux on the surface to be coated at less than about 75°, and preferably less than about 30°.

For economic reasons, the thin metal film has a thickness no greater than that needed to provide release of antimicrobial metal species on a sustainable basis over a suitable period of time, and to generate the desired interference colour. Within the preferred ranges of thicknesses set out above, the thickness will vary with the particular metal in the coating (which varies the solubility and abrasion resistance), and with the degree of atomic disorder in (and thus the solubility of) the coating. The thickness will be thin enough that the coating does not interfere with the dimensional tolerances or flexibility of the device for its intended utility.

The therapeutic effect of the material so produced is achieved when the coating is brought into contact with an alcohol or a water based electrolyte, thus releasing metal ions, atoms, molecules or clusters. The concentration of the metal species which is needed to produce a therapeutic effect will vary from metal to metal.

The ability to achieve release of metal atoms, ions, molecules or clusters on a sustainable basis from a coating is dictated by a number of factors, including coating characteristics such as composition, structure, solubility and thickness, and the nature of the environment in which the device is used. As the level of atomic disorder is increased, the amount of metal species released per unit time increases. For instance, a silver metal film deposited by magnetron sputtering at T/Tm<0.5 and a working gas pressure of about 0.93 Pa (7 mT) releases approximately ⅓ of the silver ions that a film deposited under similar conditions, but at 4 Pa (30 mT), will release over 10 days. Films that are created with an intermediate structure (ex. lower pressure, lower angle of incidence etc.) have Ag release values intermediate to these values as determined by bioassays. This then provides a method for producing controlled release metallic coatings. Slow release coatings are prepared such that the degree of disorder is low while fast release coatings are prepared such that the degree of disorder is high.

For continuous, uniform coatings, the time required for total dissolution will be a function of film thickness and the nature of the environment to which they are exposed. The relationship in respect of thickness is approximately linear, i.e. a two fold increase in film thickness will result in about a two fold increase in longevity.

It is also possible to control the metal release from a coating by forming a thin film coating with a modulated structure. For instance, a coating deposited by magnetron sputtering such that the working gas pressure was low (ex. 2 Pa or 15 mT) for 50% of the deposition time and high (ex. 4 Pa or 30 mTorr) for the remaining time, has a rapid initial release of metal ions, followed by a longer period of slow release. This type of coating is extremely effective on devices such as urinary catheters for which an initial rapid release is required to achieve immediate antimicrobial concentrations followed by a lower release rate to sustain the concentration of metal ions over a period of weeks.

The substrate temperature used during vapour deposition should not be so low that annealing or recrystallization of the coating takes place as the coating warms to ambient temperatures or the temperatures at which it is to be used (ex. body temperature). This allowable ΔT, that the temperature differential between the substrate temperature during deposition and the ultimate temperature of use, will vary from metal to metal. For the most preferred metal, Ag, preferred substrate temperatures of −20 to 200° C., more preferably −10° C. to 100° C. are used.

Atomic order may also be achieved, in either or both of the base and top layers by preparing composite metal materials, that is materials which contain one or more antimicrobial metals in a metal matrix which includes atoms or molecules different from the antimicrobial metals.

The preferred technique for preparing a composite material is to co- or sequentially deposit the antimicrobial metal(s) with one or more other inert, biocompatible metals selected from Ta, Ti, Nb, Zn, V, Hf, Mo, Si, Al and alloys of these metals or other metal elements, typically other transition metals. Such inert metals have a different atomic radii from that of the antimicrobial metals, which results in atomic disorder during deposition. Alloys of this kind can also serve to reduce atomic diffusion and thus stabilize the disordered structure. Thin film deposition equipment with multiple targets for the placement of each of the antimicrobial and biocompatible metals is preferably utilized. When layers are sequentially deposited the layer(s) of the biocompatible metal(s) should be discontinuous, for example as islands within the antimicrobial metal matrix. The final weight ratio of the antimicrobial metal(s) to biocompatible metal(s) should be greater than about 0.2. The most preferable biocompatible metals are Ti, Ta, Zn and Nb. It is also possible to form the antimicrobial coating from oxides, carbides, nitrides, sulphides, borides, halides or hydrides of one or more of the antimicrobial metals and/or one or more of the biocompatible metals to achieve the desired atomic disorder.

Another composite material may be formed by reactively co- or sequentially depositing, by physical vapour techniques, a reacted material into the thin film of the antimicrobial metal(s). The reacted material is an oxide, nitride, carbide, boride, sulphide, hydride or halide of the antimicrobial and/or biocompatible metal, formed in situ by injecting the appropriate reactants, or gases containing same, (ex. air, oxygen, water, nitrogen, hydrogen, boron, sulphur, halogens) into the deposition chamber. Atoms or molecules of these gases may also become absorbed or trapped in the metal film to create atomic disorder. The reactant may be continuously supplied during deposition for codeposition or it may be pulsed to provide for sequential deposition. The final weight ratio of reaction product to antimicrobial metal(s) should be greater than about 0.05. Air, oxygen, nitrogen and hydrogen are particularly preferred reactants, with oxygen being most preferred.

The above deposition techniques to prepare composite coatings may be used with or without the conditions of lower substrate temperatures, high working gas pressures and low angles of incidence previously discussed. One or more of these conditions are preferred to retain and enhance the amount of atomic disorder created in the coating.

The most preferred composite coatings are formed by sputtering silver, under conditions set out above, in an atmosphere containing oxygen, so as to form a coating of silver as a composite coating with oxygen.

Dressings coated with the antimicrobial coatings of this invention may be sterilized in the manner set out below.

b) Powders of Atomically Disordered Antimicrobial Metals

Crystalline powder forms of the antimicrobial or noble metals (particularly preferred being Ag, Au, Pt, and Pd) can be prepared as free standing powders, by coating powdered substrates, or from coatings on substrates which are then collected, for example by scaping and then sized. The powders may be prepared as pure metals, metal alloys or compounds such as metal oxides or metal salts, by vapour deposition, mechanical working, or compressing to impart the atomic disorder. The crystalline powders are formed with atomic disorder in accordance with the techniques set out above and as published in the prior patent applications of Burrell et al., see for example WO 93/23092, published Nov. 25, 1993, and WO 95/13704, published May 26, 1995. The atomic disorder will most typically be formed in the metal powders during physical vapour deposition as set out above for coatings or by mechanically imparting the disorder, such as by milling, grinding, hammering, mortar and pestle or compressing, under conditions of low temperature (i.e., temperatures less than the temperature of recrystallization of the material) to ensure that annealing or recyrstallization does not take place.

Alternatively, the powders may be formed by inert-gas condensation techniques, which are modified to provide atomic disorder in the powder produced, as taught in WO 95/13704 to Burrell et al.

Powders of the antimicrobial or noble metals are preferably formed by physical vapour deposition (PVD) onto a substrate such as a cold finger, a silicon wafer, solid plates, a rotating cylinder, a continuous belt in a roll coater, or on steel collectors in known PVD coaters. Preparation of powders of the present invention by sputtering onto a continuous belt in a roll coater, or other some other moving or rotating substrate surface is particularly advantageous, inasmuch as it can quickly and easily yield a relatively large supply of free-standing powder at a relatively low cost. A stainless steel belt can be used in the roll coating process without the need to provide additional cooling of the substrate. The powders or coatings and then are then scraped off to form a powder, and may be sized to avoid overly large particulates. The powders are scraped off the moving surface with scrapers which contact the moving surface at an angle sufficient to remove the coating in flake or powder form. The coating may be scraped off with scrapers angled for forward cutting of the coating from the moving surface, or with scrapers which remove the coating from the moving surface by reverse dragging action on the surface. The scrapers may be suspended above the belt, and either weighted or spring loaded to apply pressure sufficient to remove the coating from the moving surface. With a continuous belt, the scrapers can conveniently be located above the end rollers to remove the coating with a reverse dragging action as the belt rounds the end roller.

Alternatively, the powders of the antimicrobial or noble metals may be formed on powdered substrates which are biocompatible, or otherwise compatible for the end use of the powder. Particularly preferred powdered substrates are hydrocolloids, particularly those which are bioabsorbable and/or hygroscopic powders such as chitin. Exemplary bioabsorbable and/or hygroscopic powders are composed of:

Synthetic Bioabsorbable Polymers: for example polyesters/polyactones such as polymers of polyglycolic acid, glycolide, lactic acid, lactide, dioxanone, trimethylene carbonate etc., polyanhydrides, polyesteramides, polyortheoesters, polyphosphazenes, and copolymers of these and related polymers or monomers.

Naturally Derived Polymers:

Proteins: albumin, fibrin, collagen, elastin;

Polysaccharides: chitosan, alginates, hyaluronic acid; and

Biosynthetic Polyesters: 3-hydroxybutyrate polymers.

The powders may be incorporated into or onto medical dressings or pharmaceutical formulations, by any methods known in the art. For example, the powders may be layered onto the substrates (dressings or powders), mechanically fixed within the fibres of the dressings, impregnated into dressings by physical blowing, or added to topical pharmaceutical ingredients.

Preferably, powders of the present invention are sized at less than 100 $\mu$m, and more preferably less than 40 $\mu$m, and most preferably about 3–5 $\mu$m in size. For direct application to a locus of the hyperplastic tissue, tumor tissue, cancerous lesion, or other disease, powders are preferably sized less than 2 $\mu$m, and more preferably less than 1 $\mu$m.

B. Formulations for Administration

1. Coated substrates coated with antimicrobial metals formed with atomic disorder are well described above. These techniques can be used to coat dressings, meshes, films, filtering surfaces, filters, packing fibres, the insides of vials or containers etc. The coated substrates in the form of dressings for example, can be used directly on the affected area, or they can be used to generate powders, liquid or other formulations as set out below.

2. Powders of the antimicrobial metals formed with atomic disorder are set out above, and may be used in that form directly on the affected area, or in other formulations such as dressings, occlusions, creams, liquids etc. Alternatively, powders may be formulated within liquid pervious membranes such as filters, meshes and the like, such as a tea bag-type infuser, for generating liquids containing dissolved species of the antimicrobial metal.

3. Occlusions may include a hydrated dressing, with a sealing material overlaid on the outside, to the area, e.g. skin cancer or other disease, to be treated. The term hydrated dressing is meant to include non-hydrated dressings which become hydrated upon contact with an alcohol or water-based electrolyte. Occlusion prevents loss of the therapeutic agent from the area, promotes hydration of the area, and increases the temperature of the area. Examples of hydrated dressings include hydrocolloids, hydrogels, polyethylene, polyurethane, polyvinylidine, and siloxane or silicone dressings. The hydrated dressing can either be impregnated with a solution or powder of the antimicrobial metals of this invention, or can be used with a topical formulation of the antimicrobial metals of this invention.

An exemplary occlusion is a hydrocolloid dressing impregnated with silver. Alternatively, one might use a non-impregnated hydrocolloid dressing to occlude nanocrystalline silver-containing gel placed on a problematic area. A hydrocolloid is a synthetically prepared or naturally occurring polymer capable of forming a thickened gel in the presence of water and polyols (swelling agent). The swelling agent is a hydrophilic liquid capable of swelling the hydrocolloid chosen in order to form the gel phase. The hydrocolloid may be selected from the group comprising:

i representative natural or synthetically modified polysaccharides (e.g., cellulose or its derivatives such as carboxymethylcellulose, hydroxypropylcellulose, methylcellulose, hydroxypropylmethylcellulose or hydroxyethylcellulose, starch, glycogen, gelatin, pectin, chitosan and chitin; and ii representative gums from algal extracts, seed extracts, or plant exudates (e.g., gum arabic, locust bean gum, karaya gum, gum tragacanth, ghatti gum, agar-agar, carrageenans, alginates, carob gum, guar gum, xanthan gum); and iii synthetic polymers which may be either linear or crosslinked (e.g. polymers prepared from N-vinyl lactams, e.g. N-vinyl-2-pyrrolidone, 5-methyl-N-vinyl-2-pyrrolidone).

The hydrocolloid is present in an amount of from about 0.1% to 20% of the weight and preferably 1% to 10%. The hydrocolloid can range for example, from 1 to 10% of the total weight of the composition. Alternatively, the hydrocolloid may be in the form of a powder whose average particle size is less than 100 µm, preferably less than 50 µm.

The swelling agent should be non-volatile, and allow the gel to remain as a gel during use, hence preserving the swollen condition of the hydrocolloid. Varieties of non-volatile swelling agents include room temperature liquid polyols (including polyhydric alcohols) such as glycerol; room temperature solid polyols (including polyhydric alcohols) such as sorbitol, erythritol, threitol, ribotol, arabinitol, xylitol, allitol, talitol, mannitol, glucitol, glactitol, iditol, pentaerythritol, heptitol, octitol, nonitol, decitol, and dodecitol, blended with a room temperature liquid polyol; monoanhydroalditols (such as styracitol, polyalitol, D-fructose, 1,4 anhydro-D-mannitol and 1,4 anhydro-D-glucitol) blended with a room temperature liquid polyol; monosaccharides (such as pentoses, hexoses, and heptoses) blended with a room temperature liquid polyol; and ether alcohols blended with a room temperature liquid polyol.

Hydrocolloid dressings often comprise a wafer constructed from a thin layer of polyurethane film with an adhesive contact layer containing a hydrocolloid composition and securing the dressing to the area, and the polyurethane film being impermeable to water and microorganisms. Hydrocolloid dressings may be prepared by dispersing a composition in gel form of hydrocolloids with a swelling agent into a strong pressure sensitive adhesive. Alternatively, the gel and the adhesive may be mixed in a latex solution. Alternatively, exemplary products are available commercially, for example DuoDERM™ (ConvaTec Canada, 555, Dr. Frederik Philips, Suite 110, St-Laurent, Quebec, H4M 2X4); and Tegasorb™ (3M Health Care, 300 Tartan Drive, London, Ontario, Canada, N5V 4M9). The hydrocolloid dressing may be impregnated with a solution or powder of the antimicrobial metal by blending the solution or powder of the antimicrobial metal into a liquid phase during the manufacture of the hydrocolloid dressing, or by sprinkling and then pressing a powder of the antimicrobial metal into the surface of the hydrocolloid dressing. Further, the hydrocolloid dressing can be used with a topical formulation of the antimicrobial metals of this invention. Upon application, the dressing surface gels upon continued contact with moisture or exudate from the area, e.g. skin. With the incorporation of an antimicrobial metal such as silver (0.01–10%, preferably 0.1–1% by weight), the dressing is advantageous in being impermeable to water and microorganisms, and presenting antimicrobial and anti-inflammatory effects as mediated by the antimicrobial metal.

4. Gels—Nanocrystalline gels may be formed from the nanocrystalline metal powder in admixture with gelling agents such as hydrocolloids and hydrogels in powder form. Exemplary gelling agents include carboxymethyl cellulose (CMC), polyvinyl alcohol (PVA), collagen, pectin, gelatin, agarose, chitin, chitosan, and alginate, with the gelling agent comprising between about 0.01–20% w/v.

5. Creams, Lotions, Pastes, Ointments, Foams—The antimicrobial metals may be incorporated into creams, lotions, pastes, ointments or foams formulated with nanocrystalline powders or solutions of the antimicrobial metals, for example as emulsions or with drying emollients. Ointments and creams can be formulated with an aqueous or oily base with the addition of suitable thickening and/or gelling agents. Such bases may include water and/or an oil such as liquid paraffin or a vegetable oil such as peanut oil or castor oil. An exemplary base is water. Thickening agents which can be used according to the nature of the base include aluminum stearate, hydrogenated lanolin, and the like. Further, lotions can be formulated with an aqueous base and will, in general, also include one or more of the following: stabilizing agents, emulsifying agents, dispersing agents, suspending agents, thickening agents, coloring agents, perfumes, and the like. Ointments and creams can also contain excipients, such as starch, tragacanth, cellulose derivatives, polyethylene glycols, silicones, bentonites, silicic acid, and talc, or mixtures thereof. Lotions may be formulated with an aqueous or oily base and will, in general, also include one or more of the following: stabilizing agents, emulsifying agents, dispersing agents, suspending agents, thickening agents, coloring agents, perfumes, and the like. Foams may be formed with known foaming or surface active agents.

6. Liquids—The crystalline forms of the antimicrobial metals may be incorporated into liquids, formulated as solutions, dispersion or suspensions by dissolving nanocrystalline coatings or powders of the antimicrobial metals, for example as topical solutions, aerosols, mists, sprays, drops, and instillation solutions for body cavities such as the bladder, prostate, lung, or liver. Topical administration of the antimicrobial metal to the skin may be performed by aerosol, which can be generated by a nebulizer, or by instillation. The antimicrobial metal may be administered alone, or with a carrier such as saline solution, an alcohol, water, or DMSO. An effective daily amount of the antimicrobial metal will vary with the subject, but will be less than is toxic while still providing a therapeutic effect.

Solutions and formulations of the antimicrobial metals may lose some activity with aging and are thus either stabilized or generated fresh for administration. Alternatively, the antimicrobial metals may be packaged for convenient solution generation, for instance as tea bag type infusers. Other two part or two phase systems may be used in which the nanocrystalline metal is separated from the water or alcohol-based electrolyte, for example in a multicomponent kit form, as set out herein.

Concentrations of the antimicrobial metal species in solution will vary according to the application, formulation and subject, but will generally range from 1–5000 $\mu$g/ml, more preferably 20–3000 $\mu$g/ml, more preferably 40–800 $\mu$g/ml, and most preferably 50–500 $\mu$g/ml. Methods of generating liquids with appropriate concentrations of the antimicrobial metal through pH control are set out below.

7. Transdermal Patch

Transdermal patches may provide controlled delivery of the antimicrobial metal to the area. For example, an adhesive patch or adhesive matrix patch, can be prepared from a backing material and an adhesive, such as an acrylate adhesive. Powders or solutions of the antimicrobial metal may be formulated into the adhesive casting solution and allowed to mix thoroughly. The solution is cast directly onto the backing material and the casting solvent is evaporated in an oven, leaving an adhesive film. Alternatively, a polyurethane matrix patch can be employed to deliver the antimicrobial metal to the area. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and drug to the prepolymer results in the formation of a tacky firm elastomer that can be directly cast onto the backing material.

C. Sterilization

Dressings with nanocrystalline coatings of a antimicrobial metal formed with atomic disorder are preferably sterilized without applying excessive thermal energy, which can anneal out the atomic disorder, thereby reducing or eliminating a useful release of antimicrobial metal species. Gamma radiation is preferred for sterilizing such dressings, as discussed in WO 95/13704. Electron beam and ethylene oxide sterilization techniques can also be used.

It should be appreciated that the use of ultrasonic welding to laminate the layers of dressings with nanocrystalline coatings formed from antimicrobial metals with atomic disorder is advantageous since it achieves bonding in localized spots and avoids applying heat to any significant portion of the dressing, thereby avoiding any significant reduction in the solubility of the antimicrobial metals through annealing out of the atomic disorder.

The sterilized dressings, coating, powders or formulations should be sealed in packaging, containers, or kits which limit moisture and light penetration to avoid additional oxidation or reduction of the antimicrobial metal. Polyester peelable pouches are preferred. The shelf life of coatings or powders thus sealed is over one year.

D. Formulating, Dosages and Treatment

Typically, the nanocrystalline antimicrobial metals will be formulated from the active ingredient, namely nanocrystalline powders or coatings of the antimicrobial metals, or dissolved species from such powders or coatings, in the one or more of the formats set out above. Dressing or powders of the nanocrystalline antimicrobial metals may be applied directly to the hyperplastic tissue, tumor tissue, cancerous lesion, or other disease, they may be formulated as set out below. Depending on the particular application and dosage form, the powder size might be controlled to less than 2 $\mu$m, more preferably to less than 1 $\mu$m.

In the pharmaceutical compositions, the amount of the nanocrystalline metal powder may range broadly from about 0.001% to about 30% by weight, but will more preferably fall in the range of from about 0.01 to 10% by weight, and most preferably in the range of about 0.1 to 5% by weight. Typical coating thicknesses are in the range of 150 to 3000 nm thick. Thicker coatings, up to 10,000 nm thick, can be used to generate powders of the antimicrobial metal. Coatings of the nanocrystalline antimicrobial metals may be very thin, or thick, depending on the desired duration of application on the patient. As liquid formulations, the amount of dissolved antimicrobial metal will typically range between about 0.001 to 10% by weight, more preferably 0.01 to 1% by weight.

Besides the active ingredient, pharmaceutical compositions may also include non-toxic, pharmaceutically acceptable carriers, diluents and excipients, suitable for topical application, as are well known, see for example Merck Index, Merck & Co., Rahway, N.J.; and Gilman et al., (eds) (1996) Goodman and Gilman's: The Pharmacological Bases of Therapeutics, $8^{th}$ Ed., Pergamon Press. For standard dosages of conventional pharmacological agents, see, e.g., Physicians Desk Reference (1997 Edition); and U.S. Pharmacopeia National Formulary (1995) United States Pharmacopeial Convention Inc., Rockville, Md.

Dosage forms for the topical administration of compositions of the nanocrystalline antimicrobial metals include various mixtures and combinations that can be applied topically and will permit even spreading and absorption into the cutaneous surfaces. Examples include sprays, mists, aerosols, lotions, creams, solutions, gels, ointments, pastes, emulsions, foams and suspensions. The active compound can be mixed under sterile conditions with a pharmaceutically acceptable carrier, and with any preservatives, buffers, or propellants which may be required. Topical preparations can be prepared by combining the antimicrobial metal powder with conventional pharmaceutically acceptable carriers commonly used in topical dry, liquid, cream and aerosol formulations. Ointment and creams can, for example, be formulated with an aqueous or oily base with the addition of suitable thickening and/or gelling agents. An exemplary base is water. Thickening agents can be used according to the nature of the base. Lotions can be formulated with an aqueous base and will, in general, also include one or more of the following: stabilizing agents, emulsifying agents, dispersing agents, suspending agents, thickening agents, coloring agents, perfumes, and the like. Powders can be formed with the aid of any suitable powder base, e.g., talc, lactose starch and the like. Drops can be formulated with an aqueous base or non-aqueous base, and can also include one or more dispersing agents, suspending agents, solubilizing agents, surface active agents and the like.

Ointments, pastes, creams and gels also can contain excipients, such as starch, tragacanth, cellulose derivatives, silicones, bentonites, silicic acid, and talc, or mixtures thereof. Powders and sprays also can contain excipients such as lactose, talc, silicic acid, aluminum hydroxide, and calcium silicates, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such as inert gases such as nitrogen, carbon dioxide, argon or neon.

Multiple inactive ingredients are generally incorporated in topical formulations to improve cosmetic acceptability, and are optional ingredients in the formulations. Such ingredients are included only in therapeutically acceptable forms and amounts. Examples of ingredients are emulsifiers, emollients, thickening agents, solvents, hydrating or swelling agents, flavours, sweetening agents, surface active agents, colouring agents, anti-foaming agents, preservatives, fragrances, and fillers may also be added, as is well known in the art; for example, preservatives such as methyl paraben and propyl paraben, texturizing agents, thickeners, anticoagulants such as heparin, β-glucan, hormones, hyaluronic acid, and the like. Polyvinyl alcohol is a particularly preferred gelling polymer and also acts as a texturizing agent, methyl or propyl parabens are particularly preferred preservatives. These other agents may be included in amounts in the range of 0.1 to 5 wt %.

Surface active agents or foaming agents may be added to the formulations and are particularly advantageous for addition to liquid formulations for aerosol or foam applications, to form foams for applications such as to treat cancerous lesions on the skin, or aerosols for application for respiratory disorders. Surface active agents selected for use should not substantially interfere with the pro-apoptotic and anti-MMP effects of the nanocrystalline antimicrobial metals.

All agents must be non-toxic and physiologically acceptable for the intended purpose, and must not substantially interfere with the activity of the nanocrystalline antimicrobial metals so as to deleteriously affect the pro-apoptotic and anti-MMP effects. Ingredients are thus only included in therapeutically acceptable amounts. Ingredients to be generally avoided or limited in the formulations of the present invention, at least in amounts greater than 0.01 wt %, are glycerin, glycerols, chloride salts, aldehydes, ketones, long chain alcohols, and triethanolamine.

The dosage of the active ingredients depends upon many factors that are well known to those skilled in the art, for example, the particular form of the active ingredient, the condition being treated, the age, weight, and clinical condition of the recipient patient, and the experience and judgement of the clinician or practitioner administering the therapy. A therapeutically effective amount of the nanocrystalline antimicrobial metal provides either subjective relief of symptoms or an objectively identifiable improvement as noted by the clinician or other qualified observer. The dosing range varies with the metal used, its form, the route of administration and the potency of the particular compound.

When the formulation is in the form of a dressing, the dressing is placed on the affected area (e.g., cancerous lesion on the skin or locus of another disease) and, depending on the degree of moisture at the membrane, may be further moistened with drops of sterile water, tap water, body fluids such as exudate or, for example 70% ethanol, in order to activate the coating for release of antimicrobial or noble metal species. The dressing may be then secured in place with an occlusive or semi-occlusive layer, such as an adhesive tape or polyurethane film, which keeps the dressing in a moist environment. In use, the dressings are kept moist, at 100% relative humidity. Adding sterile water initially to activate the antimicrobial or noble metal coating is needed, and then as needed to maintain the dressing in a moist condition. Dressings may be changed as required for observation and cleaning. Preferably dressings are changed daily, but could be left longer, such as 3 days, and can provide a therapeutic effect for a much longer period of time.

Other forms of formulations, such as occlusions, gels, pastes, ointments, creams, emulsions, foams, and liquids may be prepared in stable forms, or more preferably are prepared fresh from one or more phases, for instance in multicomponent kit form, so as to avoid aging and to maximize the therapeutic effectiveness of the antimicrobial metal component. Formulations are best used within about 30 days after combining the phases. Suitable kits or containers are well known for maintaining the phases of formulations separate until the time of use. For instance, the antimicrobial metal in powder or coated substrate form may be packages separately from therapeutically acceptable carriers, and possibly other ingredients for mixing at the time of use. The separate coated substrate may be in dressing or patch form for direct application, or may take other suitable forms to generate liquid formulations and the like, such as a coating on the inside surface of a vial or container, a mesh, or a film. For example, the antimicrobial metal may be provided in a "tea bag"-type infuser or pouch, for generating liquid formulations at the time of use. The tea bag-type infuser is advantageous in that the pouch may serve as a filter for small particulates of the powder that may be detrimental to administration for some applications such as aerosols for respiratory disorders. A kit containing the dressing, coated substrate or powder may provide a sterile carrier such as water (and other ingredients) in a separate container in dosage specific amounts. As used herein, the term "kit" is meant to refer to packaged formulations, whether the ingredients are in separate phases or mixed, and thus for example, may include a gel in a tube with all ingredients in admixture, or any formulation wherein the ingredients are separated from each other.

Formulations for respiratory disorders may be delivered as dry powders in dry powder inhalers, or they may be formulated in liquid formulations for delivery in metered dose inhalers, aerosols, mists or sprays.

For liquid formulations, in order to increase the amount of antimicrobial or noble metal solubilized in the solution, the pH of the solution during dissolution may be lowered to less than pH 6.5, more preferably to the range of 3.5 to 6.5, with such acidifying agents as carbon dioxide (which generated carbonic acid in solution). This pH range will typically generate concentrations of silver from atomic disordered silver from 85 $\mu$g/ml to 370 $\mu$g/ml, and can be adjusted for different desired concentrations. Dissolution of the antimicrobial metal will typically raise the pH to 6.5 to 7.0.

Administration as aerosols produces droplets preferably less than 10 $\mu$m in size, more preferably less than 5 $\mu$m in size, most preferably 1–3 $\mu$m in size. Control of the droplet size is important both to control the dosage delivered and to enhance delivery to the target tissues, e.g., where the aerosol is inhaled through the mouth, large droplets of about 10 µm tend to stay in the throat whereas small droplets (e.g., approximately 1–3 µm) tend to travel to the aveolar region of the lungs. Thus, depending on the dosage required and the target tissue, it may be important to regulate the droplet size of the aerosol. In this respect, it has been found that droplet size can be regulated, to at least some extent, by the mechanical mister which is used to produce the aerosol. In addition, the aerosol's droplet size can be adjusted, to at least some extent, by modifying the surface tension of the solution. More particularly, the solution of the antimicrobial metal typically has water as its solvent, and water has a relatively high surface tension, so it is relatively straightforward to create an aerosol having relatively small droplet size. Surface active agents can be added to the solution so as to reduce the surface tension of the solution, to create an aerosol having a relatively large droplet size. By way of example, such surfactants may comprise sodium alkyl sulfates, sodium lauryl sulfate, sodium lauroyl sarconsinate, phospholipids, e.g., lecithin, sphingomyelin, etc.

Depending on the application, solutions generated from powders of the antimicrobial metal should avoid inclusion of particulates larger than 2 µm, and more preferably no larger than 1 µm (i.e., submicron) to avoid deleterious immune responses or toxic effects. Larger particulates may be removed by, for example filtration. Particulates may be formed in the liquid and can be removed, for example by filtration. For instance, silver carbonates may be formed on reaction with the carbonic acid used to acidify the solution. Particulate generation may also be limited by diluting the carbonic acid in solution.

The aerosol may be created by passing a liquid solution of the antimicrobial metal through a mechanical mister (e.g., a nebulizer) and may be applied directly with a pressurized pack (e.g., via a hand inhaler with a propellant such as carbon dioxide or other gas, with a valve metered dosage) or through some other delivery system (e.g., an oxygen tent, etc.).

The invention provides methods of treatment, by administering a therapeutically effective amount of a nanocrystalline antimicrobial or noble metal powder, or a solution derived from a nanocrystalline antimicrobial or noble metal, as either a topical formulation, or as a coating on medical dressing, applied to the locally affected area, e.g. hyperplastic tissue, tumor tissue, cancerous lesion, or locus of another disease. A therapeutically effective amount may be determined by testing formulations containing the nanocrystalline antimicrobial or noble metals by in vitro or in vivo testing. Formulations may be applied one or more times a day. Dressings coated with the nanocrystalline antimicrobial or noble metals may be changed daily, or even less frequently, and should be kept in a moist condition with the addition of saline, alcohols, or more preferably sterile water, in order to release ions, atoms, molecules or clusters of the nanocrystalline metal, on a sustained basis.

Hyperplastic tissue, tumor tissue, cancerous lesions, or other diseases may thus be treated by administering a therapeutically effective solution derived from a nanocrystalline antimicrobial or noble metal to the affected area; for example, as an infusion or instillation into a body cavity, e.g., the bladder to put the solution directly in contact with the bladder wall. Dressings or transdermal patches coated with the nanocrystalline antimicrobial metals may be applied internally in direct contact with hyperplastic tissue, tumor tissue, cancerous lesion, or a locus of another disease, and externally upon cancerous lesions, e.g., skin cancers such as melanoma, or a locus of another disease.

E. EXAMPLES

Example 1

Preparation of Nanocrystalline Silver Coatings on Dressings

This example shows the preparation of a bilayer nanocrystalline silver coating on a dressing material. A high density polyethylene dressing, DELNET™ or CONFORMANT 2™ was coated with a silver base layer and a silver/oxide top layer to generate a coloured antimicrobial coating having indicator value. The coating layers were formed by magnetron sputtering under the conditions set out in Table 1.

TABLE 1

| Sputtering conditions | | |
|---|---|---|
| Sputtering Conditions | Base Layer | Top Layer |
| Target | 99.99% Ag | 99.99% Ag |
| Target Size | 20.3 cm diameter | 20.3 cm diameter |
| Working Gas | 96/4 wt % Ar/$O_2$ | 96/4 wt % Ar/$O_2$ |
| Working Gas Pressure | 5.33 Pa (40 mT) | 5.33 Pa (40 mT) |
| Power | 0.3 kW | 0.15 kW |
| Substrate Temperature | 20° C. | 20° C. |
| Base Pressure | $3.0 \times 10^{-6}$ Torr ($4 \times 10^{-4}$ Pa) | $3.0 \times 10^{-6}$ Torr ($4 \times 10^{-4}$ Pa) |
| Anode/Cathode Distance | 100 mm | 100 mm |
| Sputtering Time | 7.5–9 min | 1.5 min |
| Voltage | 369–373 V | 346 V |

The resulting coating was blue in appearance. A fingertip touch was sufficient to cause a colour change to yellow. The base layer was about 900 nm thick, while the top layer was 100 nm thick.

To establish that silver species were released from the coated dressings, a zone of inhibition test was conducted. Mueller Hinton agar was dispensed into Petri dishes. The agar plates were allowed to surface dry prior to being inoculated with a lawn of *Staphylococcus aureus* ATCC No. 25923. The inoculant was prepared from Bactrol Discs (Difco, M.), which were reconstituted as per the manufacturer's directions. Immediately after inoculation, the coated materials to be tested were placed on the surface of the agar. The dishes were incubated for 24 hr. at 37° C. After this incubation period, the zone of inhibition was calculated (corrected zone of inhibition=zone of inhibition−diameter of the test material in contact with the agar). The results showed a corrected ZOI of about 10 mm, demonstrating good release of silver species.

The coating was analyzed by nitric acid digestion and atomic absorption analysis to contain 0.24+/−0.04 mg silver per mg high density polyethylene. The coating was a binary alloy of silver (>97%) and oxygen with negligible contaminants, based on secondary ion mass spectroscopy. The coating, as viewed by SEM, was highly porous and consisted of equiaxed nanocrystals organized into coarse columnar structures with an average grain size of 10 nm. Silver release studies in water demonstrated that silver was released continuously from the coating until an equilibrium concentration of about 66 mg/L was reached (determined by atomic absorption), a level that is 50 to 100 times higher than is expected from bulk silver metal (solubility≦1 mg/L).

By varying the coating conditions for the top layer to lengthen the sputtering time to 2 min, 15 sec., a yellow coating was produced. The top layer had a thickness of about 140 nm and went through a colour change to purple with a fingertip touch. Similarly, a purple coating was produced by shortening the sputtering time to 1 min, to achieve a top layer thickness of about 65 nm. A fingertip touch caused a colour change to yellow.

To form a three layer dressing, two layers of this coated dressing material were placed above and below an absorbent core material formed from needle punched rayon/polyester (SONTARA™ 8411). With the silver coating on both the first and third layers, the dressing may be used with either the blue coating side or the silver side in the skin facing position. For indicator value, it might be preferable to have the blue coating visible. The three layers were laminated together by ultasonic welding to produce welds between all three layers spaced at about 2.5 cm intervals across the dressing. This allowed the dressing to be cut down to about 2.5 cm size portions for smaller dressing needs while still providing at least one weld in the dressing portion.

The coated dressings were sterilized using gamma radiation and a sterilization dose of 25 kGy. The finished dressing was packaged individually in sealed polyester peelable pouches, and has shown a shelf life greater than 1 year in this form. The coated dressings can be cut in ready to use sizes, such as 5.1×10.2 cm strips, before packaging. Alternatively, the dressings may be packaged with instructions for the patient or clinician to cut the dressing to size.

Additional silver coated dressings were prepared in a full scale roll coater under conditions to provide coatings having the same properties set out above, as follows:

i the dressing material included a first layer of silver coated DELNET, as set out above, laminated to STRATEX, AET, 8.0NP$_2$-A/QW, which is a layer of 100% rayon on a polyurethane film.

ii Silver Foam Dressing—three layers of silver coated high density polyethylene prepared as above, alternating with two layers of polyurethane foam, L-00562-6 Medical Foam, available from Rynel Ltd., Bootbay, Me., USA.

Example 2

Preparation of Atomic Disordered Nanocrystalline Silver Powders

Nanocrystalline silver coatings were prepared by sputtering silver in an oxygen-containing atmosphere directly onto an endless stainless steel belt of a magnetron sputtering roll coater, or onto silicon wafers on the belt. The belt did not need to be cooled. The coatings were scraped off with the belt with suspended metal scrapers as the belt rounded the end rollers. For the coated silicon wafers, the coatings were scraped off with a knife edge. The sputtering conditions were as follows:

TABLE 2

| Sputtering Conditions | |
|---|---|
| Target | 99.99% Ag |
| Target Size (individual, 23 targets) | 15.24 cm × 1216.125 cm |
| Working Gas | 75:25 wt % Ar/O$_2$ |
| Working Gas Pressure | 5.33 Pa (40 mT) |
| Total Current | 40 A |
| Base Pressure | 5.0 × 10$^{-5}$ Torr (range: 1 × 10$^{-4}$–9 × 10$^{-7}$ Torr or 1 × 10$^{-2}$–1.2 × 10$^{-4}$ Pa) |

TABLE 2-continued

| Sputtering Conditions | |
|---|---|
| Target | 99.99% Ag |
| Sandvik Belt Speed | 340 mm/min |
| Voltage | 370 V |

Note - pressure conversions to Pa herein may not be accurate, most accurate numbers are in torr, mTorr units.

The powder had a particle size ranging from 2 μm to 100 μm, with grain or crystallite size of 8 to 10 nm (i.e., nanocrystalline), and demonstrated a positive rest potential.

Similar atomic disordered nanocrystalline silver powders were formed as set forth hereinabove by magnetron sputtering onto cooled steel collectors, under conditions taught in the prior Burrell et al. patents to produce atomic disorder.

Example 3

Preparation of Gels

No. 1

A commercial carboxymethyl cellulose/pectin gel (Duo-DERM™, ConvaTec Canada, 555, Dr. Frederik Philips, Suite 110, St-Laurent, Quebec, H4M 2X4) was combined with nanocrystalline silver powder prepared as set forth in Example 3 to produce a gel with 0.1% silver. A logarithmic reduction test was performed as follows in the gel using *Pseudomonas aeruginosa*. The inoculum was prepared by placing 1 bacteriologic loopful of the organism in 5 mL of trypticase soy broth and incubating it for 3–4 h. The inoculum (0.1 mL) was then added to 0.1 mL of gel and vortexed (triplicate samples). The mixture was incubated for one-half hour. Then 1.8 mL of sodium thioglycollate-saline (STS) solution was added to the test tube and vortexed. Serial dilutions were prepared on 10$^{-1}$ to 10$^{-7}$. A 0.1 mL aliquot of each dilution was plated in duplicate into Petri plates containing Mueller-Hinton agar. The plates were incubated for 48 h and then colonies were counted. Surviving members of organisms were determined and the logarithmic reduction compared to the initial inoculum was calculated. The logarithmic reduction for this mixture was 6.2, indicating a significant bactericidal effect.

No. 2

Carboxymethyl cellulose (CMC) fibers were coated directly to produce an atomic disordered nanocrystalline silver coating, using magnetron sputtering conditions similar to those set forth in Example 1. The CMC was then gelled in water by adding 2.9 g to 100 mL volume. This material was tested using the method of No. 1. The material generated a 5.2 logarithmic reduction of *Pseudomonas aeruginosa*, demonstrating that the gel had a significant bactericidal effect.

No. 3

An alginate fibrous substrate was directly coated with an atomic disordered nanocrystalline silver coating using magnetron sputtering conditions similar to those set forth in Example 1. The alginate (5.7 g) was added to 100 mL volume of water to create a gel. This material was tested using the method of No. 1. The material generated a 5.2 logarithmic reduction of *Pseudomonas aeruginosa*, demonstrating that the gel had a significant bactericidal effect.

No. 4

A commercial gel containing CMC and alginate (Purilin gel, Coloplast) was mixed with a atomic disordered nanocrystalline silver powder to give a product with 0.1% silver. This was tested as above with both *Pseudomonas aeruginosa* and *Staphylococcus aureus*. Zone of inhibition data was also generated for this gel as follows. An inoculum (*Pseudomonas aeruginosa* and *Staphylococcus aureus*) was prepared as in No. 1 and 0.1 mL of this was spread onto the surface of Mueller-Hinton agar in a Petri dish. A six mm hole was then cut into the agar at the center of the Petri dish and removed. The well was filled with either 0.1 mL of the silver containing gel, a mupirocin containing cream or a mupirocin containing ointment. The Petri plates were then incubated for 24 h and the diameter of the zone of inhibition was measured and recorded.

The silver containing gel produced 9 mm zone of inhibition against both *Pseudomonas aeruginosa* and *Staphylococcus aureus*, while the mupirocin cream and ointment produced 42 and 48 mm zones against *Staphylococcus aureus* and 0 mm zones against *Pseudomonas aeruginosa*.

The silver containing gel reduced the *Pseudomonas aeruginosa* and *Staphylococcus aureus* properties by 4.4 and 0.6 log reductions, respectively, showing good bactericidal activity. The mupirocin cream and ointment generated 0.4 and 0.8, and 0.8 and 1.6, log reductions against *Staphylococcus aureus* and *Pseudomonas aeruginosa*, respectively. The silver gel had both a greater bactericidal effect and spectrum of activity than the mupirocin containing products.

Nos. 5–10

The formula for Nos. 5–10 are summarized in Table 7. Zones of inhibitions were determined as in No. 4 and log reductions were determined as in No. 1.

All formulae provided a broader spectrum of activity and a greater bactericidal effect than did mupirocin in a cream or ointment form. The mupirocin cream produced zones of inhibition of 42 and 0, and log reduction of 0.4 and 0.8, against *Staphylococcus aureus* and *Pseudomonas aeruginosa*, respectively.

Example 4

Effects of Antimicrobial Silver on Apoptosis and Matrix Metalloproteinases in a Porcine Model A porcine model was used to examine the effects of an antimicrobial metal formed with atomic disorder, preferably silver, on apoptosis and matrix metalloproteinases. Young, commercially produced, specific pathogen free domestic swine (20–25 kg) were used in these studies. The animals were conditioned in an animal facility for one week prior to any experimental manipulation. Typically, three animals were used in each experiment. The animals received water and hog ration (Unifeed™, Calgary, Alberta) without antibiotics ad libitum, were housed individually in suspended stainless steel cages (5'×6'), and maintained in a controlled environment with 12 hours of light per day. The study was approved by the University of Calgary Animal Care Committee and was conducted in accordance with guidelines established by the Canadian Council on Animal Care.

Antimicrobial silver metal was administered in the form of a dressing. The dressings included:

i) AB—nanocrystalline silver-coated dressing (the non-foam, three-layer dressing as set out in Example 1), comprising two layers of silver-coated high density polyethylene (HDPE) bonded on either side of an absorbent rayon/polyester core;

ii) AgHDPE—nanocrystalline silver coated HDPE layers aseptically separated from the absorbent core of the AB dressings;

iii) Control—identical in construction to the AB dressing except that the HDPE was not coated with nanocrystalline silver;

iv) Gauze—the absorbent rayon/polyester core of the AB dressings;

v) cHDPE—the uncoated HDPE aseptically removed from the absorbent core of the control dressings; and

TABLE 3

Formulae for Gel Nos. 5–10 and Efficacy Results

| # | CMC (%) | PVA (%) | Silver Powder (%) | β-glucan | Methyl paraben | Propyl paraben | CZOI *S. Aureus* | CZOI *P. aeruginosa* | Log Red'n *S. aureus* | Log Red'n *P. aeruginosa* |
|---|---|---|---|---|---|---|---|---|---|---|
| 5 | 2 |  | 0.1 |  |  |  | 11 | 13 | 1.4 | >6 |
| 6 | 2 | 0.5 | 0.1 |  | 0.1 | 0.02 | 14 | 15 | 3.3 | >6 |
| 7 | 2 | 0.5 | 0.1 |  |  |  | 13 | 14 | 2 | N/A |
| 8 | 2 | 0.5 | 0.1 |  | 0.1 |  | 14 | 14 | 2 | N/A |
| 9 | 2 | 0.5 | 0.1 |  |  | 0.20 | 14 | 14 | 2 | N/A |
| 10 | 2 | 0.5 | 0.1 | 0.5 | 0.1 | 0.20 | 14 | 14 | 2 | >6 |

No. 11

A commercially available gel (glyceryl polymethacrylate) was blended with nanocrystalline silver powder of Example 3 to produce a gel with a silver content of 0.1%. This gel was tested as in Nos. 5–10 and was found to produce zones of 15 mm against both *Staphylococcus aureus* and *Pseudomonas aeruginosa*. Log reductions of 1.7 and >5 were produced against *Staphylococcus aureus* and *Pseudomonas aeruginosa*. This gel product had a greater spectrum of activity than did mupirocin cream or ointment.

Testing of the above preparations for antimicrobial effect was conducted to ensure that the antimicrobial metals, such as the nanocrystalline silver in these gels, are effectively released.

vi) SN—sterile piece of the gauze dressing to which 24 μg silver/square inch (from silver nitrate) was added. This amount of silver is equivalent to the amount of silver released from a square inch of the AB dressing immersed in serum over a 24 hour period, as determined by atomic absorption analysis.

Dressings (i)–(iii) were gamma sterilized (25 kGy) prior to use. All dressings were moistened with sterile water prior to application to the incision. In some cases, the incisions were covered with a layer of occlusive polyurethane (Tegaderm™, 3M Corp., Minneapolis, Minn.).

Three isolates of bacteria were used in the inoculum, including *Pseudomonas aeruginosa*, *Fusobacterium* sp., and coagulase-negative *staphylococci* (CNS) (Culture Collection, University of Calgary, Calgary, Alberta). The bacterial strains were grown under appropriate conditions overnight prior to the day of surgery. On the morning of surgery, the organisms were washed with sterile water and resuspended to a final density of approximately $10^7$ CFU/mL. The bacteria were mixed together in a ratio of 1:0.5:1 (*Pseudomonas*:CNS:*Fusobacterium*) in water. Sufficient inoculum was prepared to wet the incision created in each experiment. This procedure resulted in the incisions initially being evenly contaminated with approximately $8\times10^4$ CFU/cm$^2$.

Prior to treatment, animals were sedated by an intramuscular injection of a mixture of 10 mg/kg ketamine (Ketalean™, MTC Pharmaceuticals, Cambridge, ON) and 0.2 mg/kg acepromazine (Atravet™, Ayerst Laboratories), followed by complete anesthesia induced by mask inhalation of 1–2% halothane (MTC Pharmaceuticals). Following induction of anesthesia, the dorsal and lateral thorax and abdomen of each animal was clipped using a #40 Osler blade and the skin subsequently scrubbed with a non-antibiotic soap, and allowed to dry prior to incision.

Animals typically received 20 full-thickness incisions, 10 on each side of the dorsal thorax. The incisions were created using a 2 cm diameter trephine. An epinephrine solution was then applied to the incisions to provide for complete hemostasis prior to inoculation. The incisions were contaminated by covering them with gauze sponges soaked with the bacterial inoculum. The wet sponges were covered with an occlusive barrier and allowed to stand for 15 minutes. In some instances, an incision was then sampled to determine the initial inoculum. Following any requisite sampling, the incisions were dressed with the appropriate dressings and covered with an occlusive layer that was secured with Elastoplast™ tape (Smith & Nephew, Lachine, QC). All animals received narcotic pain medication (Torbugesic™, Ayerst Laboratories, Montreal, QC, 0.2 mg/kg), as required.

The experimental and control groups are summarized in Table 4:

TABLE 4

Experimental and Control Groups

| Animal # | Left Side (Silver Treatment) | Right Side (Controls) |
| --- | --- | --- |
| Pig 1 | Silver nitrate (SN) on gauze | gauze moistened with water |
| Pig 2 | AgHDPE | cHDPE |
| Pig 3 | AB | control |

A 2 cm diameter circle of the appropriate dressing was applied to each incision. For Pig 1, incisions on the left side were dressed with silver nitrate-moistened (SN) gauze, while control incisions on the right side received water-moistened gauze dressing. For Pig 2, the incisions on the left side were dressed with silver-coated HDPE (AgHDPE), while the control incisions on the right side received non-coated HDPE (cHDPE). For Pig 3, the incisions on the left side were dressed with AB dressing, while incisions on the right side received the vehicle control. For these experiments, each incision was individually covered with an occlusive film dressing (Tegaderm™, 3M Corp., Minneapolis, Minn.).

Each day following incision (up to 5 days), the dressing materials from each of the experimental and control groups were collected and pooled within each group. These dressing materials were then placed in conical centrifuge tube containing glass wool. The tubes and contents were centrifuged to remove all liquid from the dressings. The glass wool was then placed into a 5-mL syringe and pressed to recover the incision fluid from each of the six sample sets. The incisions were rebandaged in an identical manner to the original dressing format each time. Incision fluid which collected under the occlusive dressing was also aspirated and reserved for analysis. Due to the small volumes collected from each incision, it was necessary to pool the collected fluid from each of 10 incisions dressed with the same type of dressing. All incision fluids were stored at −80° C. until analysis.

Prior to enzyme zymography or activity assays, the protein concentrations of the incision fluid samples were compared to ensure that the protein levels in each sample were similar. The samples were diluted 1:100 in water and assayed using the BCA Protein Assay System™ (Pierce Chemical, Rockford, Ill.). A standard curve was concurrently constructed using dilutions of bovine serum albumin. Incision fluid was diluted in water and then mixed with an equal volume of sample buffer (0.06 M Tris-HCl, pH 6.8; 12% SDS; 10% glycerol; 0.005% bromophenol blue). The samples were then electrophoresed on 10% polyacrylamide (BioRad, Mississauga, ON) gels containing 0.1% gelatin. The proteins were then incubated in renaturing buffer (2.5% Triton™ X-100) for 90 minutes at 37° C. Following enzyme renaturation, the gels were incubated overnight in substrate buffer (50 mM Tri-HCl, pH 7.8; 5 mM $CaCl_2$; 200 mM NaCl; 0.02% Brij-35) with or without 10 mM 1,10 phenanthroline. The gels were subsequently stained with a standard Coomassie Blue stain and destained in methanol/acetic acid. Unless otherwise indicated, all chemicals were obtained from Sigma-Aldrich (Oakville, ON).

The incision fluid samples were assayed for the total amount of protein present. These values were between 30–80 mg/mL. The samples from individual animals were even more similar, varying by only 10–20 mg/mL in the pooled incision fluid.

i) Assay for Activity of Total MMPs

The total MMP activity of the incision fluid samples was determined by incubating diluted incision fluid with a quenched fluorescein-conjugated substrate (EnzChek DQ gelatin™, Molecular Probes, Eugene, Oreg.) for approximately 20 hours. Following incubation, the samples were read in a fluorometer (excitation 1=480 nm; emission 1=520 nm). Activity was compared to a collagenase standard as well as experimental versus control incision fluids.

FIG. 1 shows the change in total MMP activity from differently treated incision sites over a five-day period. The silver-coated HDPE (AgHDPE) results were essentially identical to those obtained using the silver-coated dressing (AB). Similarly, the gauze, non-coated HDPE (cHDPE), and control dressings yielded results essentially identical to each other and to untreated incisions under occlusion from which incision fluid was collected. Only the results from the control, silver-coated dressing (AB), silver-coated HDPE (AgHDPE), and silver nitrate moistened gauze (SN) are thus shown. The total MMP activity of the incision fluid sample from the control dressing was low for the first few days, then rose dramatically and remained high for the duration of the experiment. Similarly, the silver-nitrate moistened gauze (SN) demonstrated an almost identical pattern of total MMP activity. Results from the silver-coated dressing (AB) yielded dramatically different results. The level of MMP activity remained steady for the duration of the experiment and did not spike to high levels. Instead, it remained at a level roughly 60% lower than the highest level of activity reached in control or silver-nitrate moistened gauze (SN).

ii) Assay for Activity of Gelatinases

Gelatinases include MMP-2 (secreted by fibroblasts and a wide variety of other cell types) and MMP-9 (released by mononuclear phagocytes, neutrophils, corneal epithelial cells, tumor cells, cytotrophoblasts and keratinocytes). The gelatinases degrade gelatins (denatured collagens) and collagen type IV (basement membrane). Zymograms were run to examine changes in the levels and activity of MMP-9 and MMP-2 over the duration of the experiment.

Results of the zymograms for the control and silver nitrate moistened gauze (SN) appeared to be identical. The levels of MMP-9 declined over the period examined, particularly levels of the active form of MMP-9. The silver-coated dressing (AB) demonstrated higher levels of active MMP-9 than for the control. On Day 2, the silver-coated dressing (AB) showed lower levels of active MMP-9 than in the control. On Day 4, the silver-coated dressing (AB) showed little active MMP-9. In the control, the amount of the latent enzyme appeared to decrease while the active form of MMP-9 increased, particularly up to Day 4.

There was not much difference in the levels of MMP-2 activity for the silver-coated dressing (AB) over the duration of the experiment. However, there was an increase in the level of active MMP-2 in the control dressing by Day 5. It was also observed that the levels of some other, unidentified, gelatinolytic enzymes also decreased in the silver-coated dressing (AB) compared to the control.

iii) Assay of Total Protease Activity

Since MMPs have proteolytic activity, the total protease activity in incision fluid samples was assessed by incubating the samples with 3 mg/mL azocasein in 0.05 M Tris-HCl, pH 7.5 for 24 hours at 37° C. The undigested substrate was then precipitated by the addition of 20% trichloroacetic acid. The absorbance of the supernatant was then assessed using a spectrophotometer, $l=400$ nm. The absorbance was compared to a standard curve prepared with bovine pancreatic trypsin.

Figure 2:
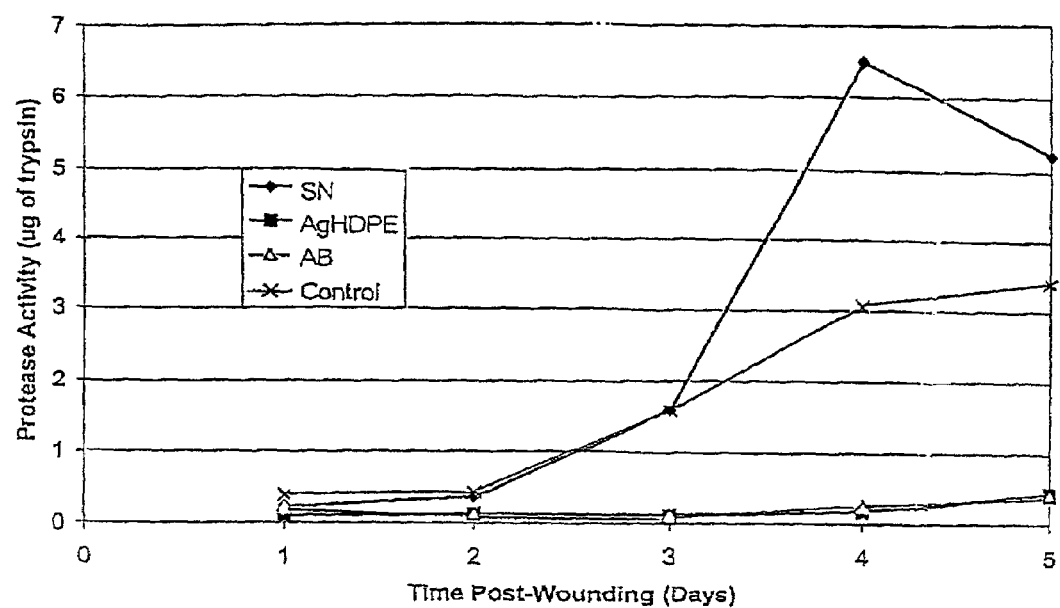
FIG. 2 is a graph showing total protease activity of incision fluids recovered from the silver-coated dressing (AB), silver nitrate moistened gauze (SN dressing), silver-coated AgHDPE, and control dressing over a duration of 5 days.

Results paralleled those obtained in the total MMP assay above. The incision fluid samples for the control and silver nitrate moistened gauze (SN) demonstrated a pronounced increase in activity after Day 2 (FIG. 2). Incision fluid from the silver nitrate moistened gauze (SN) also demonstrated a marked increase in the total protease activity compared to control dressing incision fluid (FIG. 1). However, the total protease activity in the incision fluids of the silver coated dressings (AB) remained constant over the duration of the experiment.

Antimicrobial silver was thus demonstrated to be effective in modulating overall MMP activity. However, silver nitrate was not effective in modulating MMP activity in spite of the $Ag^+$ concentration being approximately the same levels as were expected to be released from the silver-coated dressing (AB) over the same period of time (24 h) between applications. The reason for the difference in effects may be related to the inherent nature of the two silver formulations. In the case of silver nitrate, although the silver was added to provide a similar final concentration of $Ag^+$ as was anticipated to be released from the silver-coated dressing (AB), the $Ag^+$ ions were added at once. It would thus be expected that the serum proteins and chlorides within the incision fluid would quickly inactivate a large portion of the $Ag^+$. In the case of the silver-coated dressing (AB), the silver is continuously released to maintain a steady-state equilibrium, maintaining an effective level of silver in the incision for a prolonged period.

iv) Apoptosis

Histological assessment of cell apoptosis was carried out in order to determine whether the silver-coated dressing (AB) affected apoptosis within the incision.

Histological Observations of Porcine Tissue

Samples of tissue from the incisions were collected daily for the duration of the experiment, except for Day 1, and examined for evidence of apoptosis. The samples were fixed in 3.7% formaldehyde in PBS for 24 hours, then embedded in paraffin, and cut into 5 mm thick sections. The samples were then de-waxed with Clearing Solvent™ (Stephan's Scientific, Riverdale, N.J.) and rehydrated through an ethanol:water dilution series. The sections were treated with 20 mg/mL proteinase K (Qiagen, Germantown, Md.) in 10 mM Tris-HCl (pH 7.4) for 30 minutes at room temperature.

Terminal deoxynucleotidyl transferase nick end labeling (TUNEL staining) was performed using an In Situ Cell Death Detection POD Kit™ (Boehringer Mannheim, Indianapolis, Ind.). Using this technique, cells which stain brown are those being eliminated by apoptosis. Endogenous peroxidase was blocked with 3% hydrogen peroxide in methanol for 10 minutes at room temperature then cells were permeabilized with 0.1% Triton™ X-100 (in 0.1% sodium citrate) for 2 minutes on ice. After permeabilization, the samples were treated with the terminal transferase enzyme solution incubated in a humidified chamber at 37° C. for 60 minutes. Following labelling, the samples were washed once with 1.0% Triton™ X-100 and twice with PBS. The sections were incubated with Converter-POD™ (Boehringer Mannheim, Indianapolis, Ind.) in a humidified chamber at 37° C. for 30 minutes, and repeated washing with 1.0% Triton™ X-100 and PBS. Subsequently, the samples were incubated with DAB substrate (Vector Laboratory Inc., Burlingame, Calif.) for 10 minutes at room temperature and washed with 1.0% Triton™ X-100 and PBS. It was also necessary to counterstain the sections with hematoxylin nuclear counterstain (Vector Laboratory Inc., Burlingame, Calif.) for 10 seconds.

The prepared samples were then ready to be observed by light microscopy for evidence of apoptosis. For a positive control, the permeabilized sections were treated with 100 mg/mL DNase I in PBS for 10 minutes at room temperature to induce DNA strand breaks. For negative controls, the terminal transferase enzyme, POD or DAB were omitted between each labelling step.

In all samples examined, there was little difference between the control and silver nitrate moistened gauze (SN). However, significant apoptosis of the cell population was observed in incisions of the silver-coated dressing (AB). In the control incision, there were significant numbers of polymorphonuclear leukocytes (PMNs) and few fibroblasts, while in incisions of the silver-coated dressing (AB), there were significantly more fibroblasts and few PMNs.

Histopathological Scoring of Porcine Tissue

Animals were anesthetized as described above of Days 1, 4, and 7. A mid-incision biopsy was collected with a sterile 4 mm biopsy punch. The tissue was fixed in 10% neutral buffered formalin, embedded in methacrylate and sectioned (2–5 mm thick). The sections were stained with Lee's methylene blue and basic fuschin to demonstrate the cellular organization and bacteria. A pathologist blinded to the treatments scored the sections based on the presence of fibroblasts, PMNs and bacteria as follows: 0=absent; +=occasional with 1–5 per high power field of view; ++=moderate with 6–20 per high power field of view;

+++=abundant with 21–50 per high power field of view;
++++=very abundant with more than 50 per high power field of view (Table 5).

TABLE 5

Histopathological Scoring of Porcine Tissue Collected on Days 1, 4 and 7

| Day Post-incision | Dressing | Fibroblasts | PMNs | Bacteria |
|---|---|---|---|---|
| 1 | Silver-coated (AB) | ++ | ++ | + |
| 1 | Control | 0 | +++ | ++++ |
| 4 | Silver-coated (AB) | ++++ | ++ | 0 |
| 4 | Control | + | ++++ | ++++ |
| 7 | Silver-coated (AB) | ++++ | + | 0 |
| 7 | Control | +++ | +++ | +++ |

The microscopic observation of the biopsy samples revealed that the infiltrating cell types were significantly different between the control and silver-coated dressings (AB). The control incisions were characterized by a large numbers of PMNs, while the silver-coated dressings (AB) demonstrated a larger proportion of fibroblasts and monocytes. The relative abundance of the fibroblasts in incisions of the silver-coated dressings (AB) became increasingly pronounced through to Day 7, as compared to the control incisions that remained populated largely by PMNs and monocytes. The staining method enabled staining also of bacteria, which was abundant in the control incision but generally absent in the incisions of the silver-coated dressings (AB).

Incisions treated with the nanocrystalline antimicrobial silver thus demonstrated more extensive apoptosis than did cells from incisions treated with either control or silver nitrate dressings. During the first two days following incision, the cell type which demonstrated the most pronounced increase in apoptosis were neutrophils. This suggests that part of the reason for the moderated neutrophil presence and the resultant modulation of MMP levels was due to neutrophil apoptosis. It has been shown that the number of apoptotic cells increases as the incision closes and that this is part of the mechanism involved in the decrease in cellularity of the maturing scar tissue (Desmouliere, A., Badid, C., Bochaton-Piallat, M. and Gabbiani, G. (1997) Apoptosis during wound healing, fibrocontractive diseases and vascular wall injury. *Int. J. Biochem. Cell Biol.* 29: 19–30.). The results suggest that the maturing of the nascent dermal and epidermal tissues may also be accelerated in the presence of the nanocrystalline antimicrobial metals. The findings indicated that acceleration in healing induced by the nanocrystalline antimicrobial metals is associated with a reduction of local MMP activity, as well as with an increased incidence of cell apoptosis within the incision.

Example 5

Clinical Study on the Effect of Silver-Coated Dressings on MMPs and Cytokines

This study was conducted to assess the effect of the silver-coated dressing on the concentrations of MMPs and cytokines in non-healing wounds over time during treatment. The modulation of the levels of active MMPs and cytokines may alleviate the inflammatory response in a wound, allowing the wound to advance through the subsequent stages of wound healing culminating in a healed wound.

A total of 10 patients with non-healing venous stasis ulcers were randomly assigned to treatment with a silver-coated dressing (5 patients) or a control dressing (5 patients). The silver-coated dressing was prepared as in Example 1. The control dressing was identical in construction to the silver-coated dressing of Example 1, except that the HDPE was not coated with silver. The ulcers were dressed in appropriate pressure dressings to correct the underlying medical problem. Samples of the ulcer fluid were collected before treatment (day 0) and at weekly intervals (days 1, 7, 14 and 21) by removing the silver-coated dressing or control dressing, and replacing the dressing with Tegaderm™ occlusive dressing (3M Corp., Minneapolis, Minn.) for one hour to allow wound fluids to collect. The fluid samples were aspirated from below the dressing in a syringe, and were frozen at −80° C. until assayed.

Assays were conducted for active MMP-9, active MMP-2, Tumor necrosis factor-α (TNF-α) and Interleukin-1β (IL-1β). High levels of MMP-9 and MMP-2 are predominant in non-healing wounds, with levels decreasing over time in normal healing wounds. Released by activated macrophages, TNF-α and IL-1β are indicators of wound inflammation. Levels of TNF-α and IL-1β are elevated in non-healing wounds and increase release of pro-MMPs, for example, MMP-9 and MMP-2.

To measure the levels of active MMP-9 and MMP-2, enzyme capture assays (BioTrak, N.J.) were conducted. In this method, active enzyme is detected through activation of a modified pro-detection enzyme and the cleavage of its chromogenic peptide substrate. The resultant color is read by spectrophotometer, and the concentration of MMP is determined by interpolation of a standard curve, expressed in ng/ml (see results in FIGS. 3 and 4).

To assay the levels of cytokines, IL-1β levels were measured using a sandwich immunoassay (BioTrak, N.J.), while TNF-α levels were measured by a high sensitivity sandwich antibody assay (BioTrak, N.J.). In both methods, endogenous cytokine is bound to an immobilized antibody and then detected by an addition of a biotinylated antibody, followed by a colorimetric substrate. The color is measured by a spectrophotometer, and the concentrations of TNF-α and IL-1β are determined by interpolation of a standard curve and expressed as pg/ml (see results in FIGS. 5 and 6).

Total protein levels were measured for each sample to standardize the measures of the MMPs and cytokines. Total protein levels were measured using BCA Protein Assay System™ (Pierce Chemical, Rockford, Ill.). No protein level of any sample was significantly different from the total mean.

Figure 3:
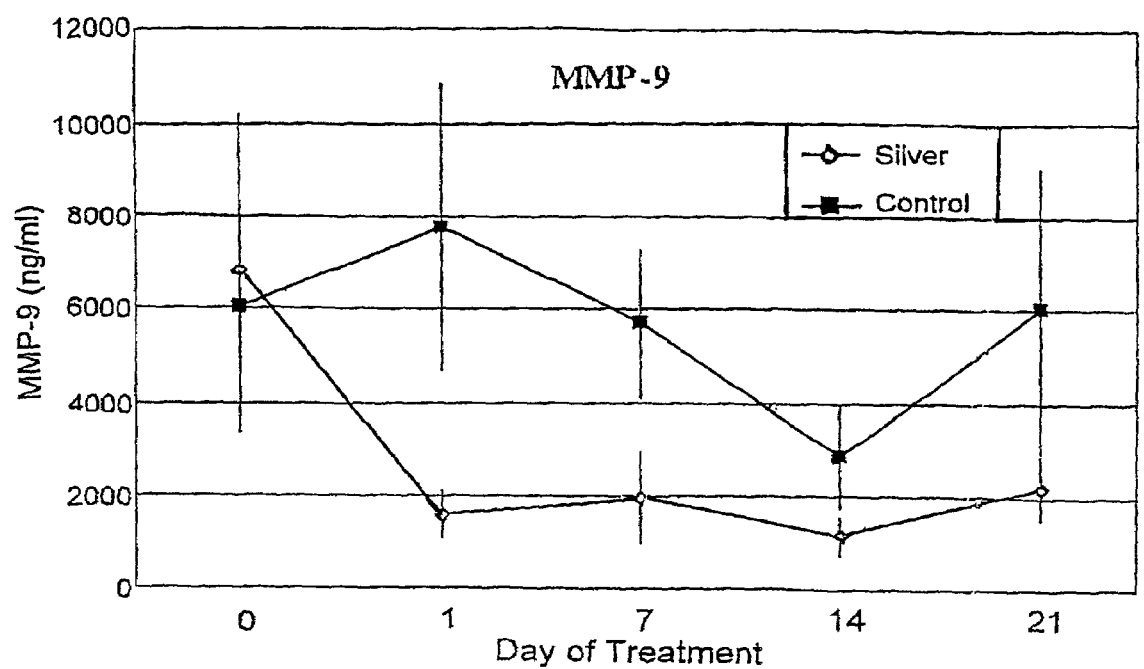
FIG. 3 is a graph showing the concentrations (ng/ml) of active MMP-9 in fluid samples recovered from ulcers dressed with silver-coated dressing (Silver) and control dressing (Control) at days 0, 1, 7, 14 and 21.

FIG. 3 is a graph showing the concentrations (ng/ml) of active MMP-9 in fluid samples recovered from ulcers dressed with silver-coated dressing (Silver) and control dressing (Control) at days 0, 1, 7, 14 and 21. The levels of active MMP-9 decreased to a normal level, and were suppressed over time with the silver-coated dressing compared to the control dressing, demonstrating a modulating effect of the silver-coated dressing.

Figure 4:
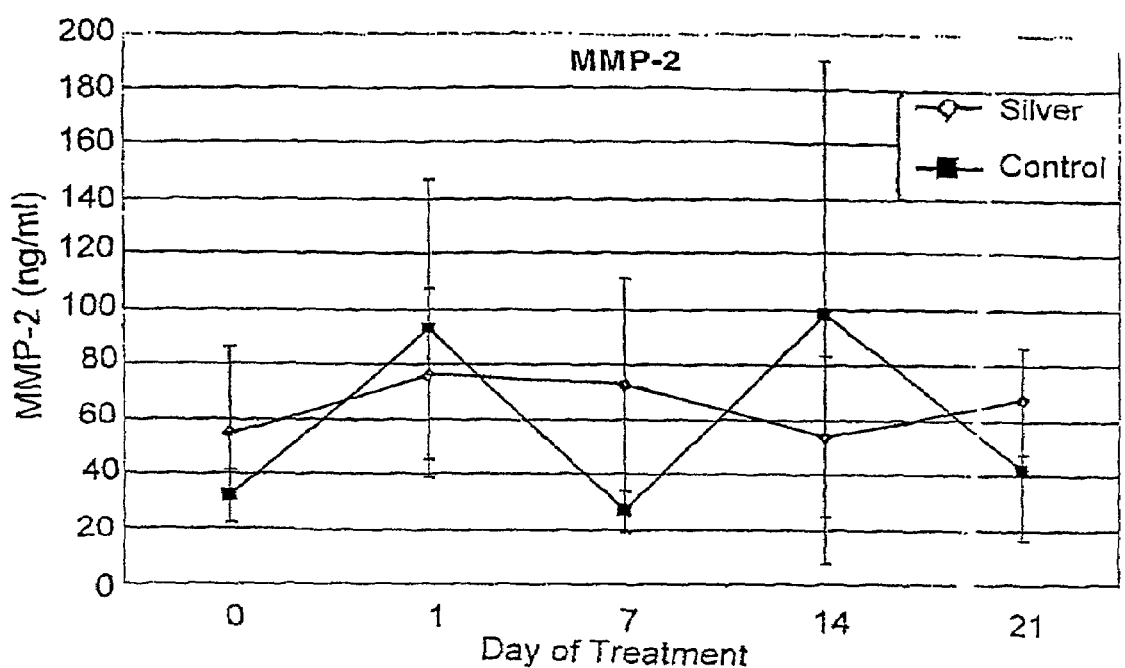
FIG. 4 is a graph showing the concentrations (ng/ml) of active MMP-2 in fluid samples recovered from ulcers dressed with silver-coated dressing (Silver) and control dressing (Control) at days 0, 1, 7, 14 and 21.

FIG. 4 is a graph showing the concentrations (ng/ml) of active MMP-2 in fluid samples recovered from ulcers dressed with silver-coated dressing (Silver) and control dressing (Control) at days 0, 1, 7, 14 and 21. The levels of active MMP-2 were not significantly different with the silver-coated dressing and the control dressing.

Figure 5:
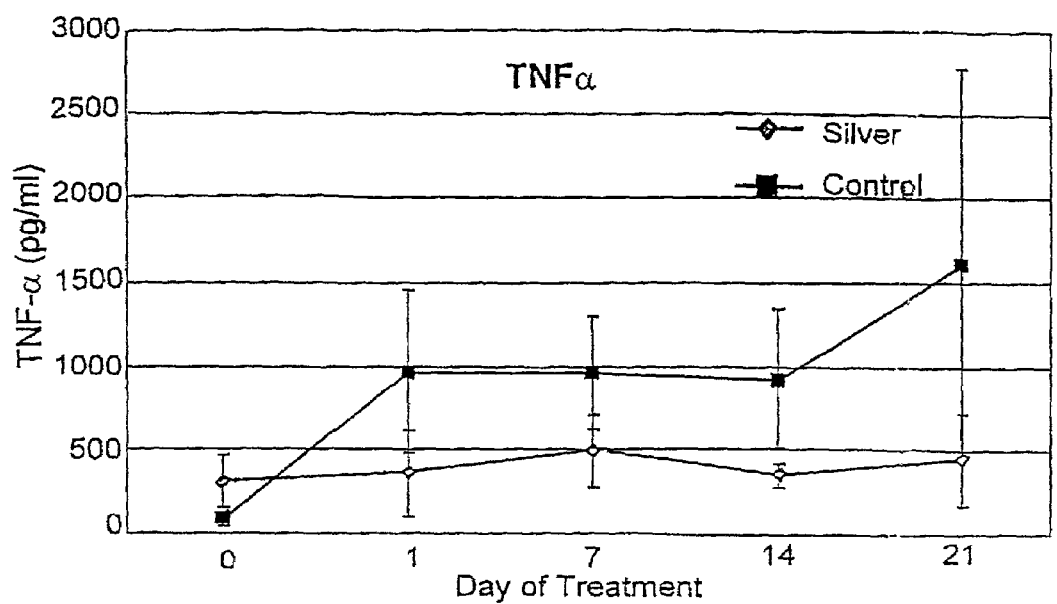
FIG. 5 is a graph showing the concentrations (pg/ml) of TNF-$\alpha$ in fluid samples recovered from ulcers dressed with silver-coated dressing (Silver) and control dressing (Control) at days 0, 1, 7, 14 and 21.

FIG. 5 is a graph showing the concentrations (pg/ml) of TNF-α in fluid samples recovered from ulcers dressed with silver-coated dressing (Silver) and control dressing (Control) at days 0, 1, 7, 14 and 21. The levels of TNF-α were suppressed over the treatment period, and did not increase significantly over the treatment period with the silver-coated dressing, while the levels in the control dressing increased, demonstrating a modulating effect of the silver-coated dressing.

Figure 6:
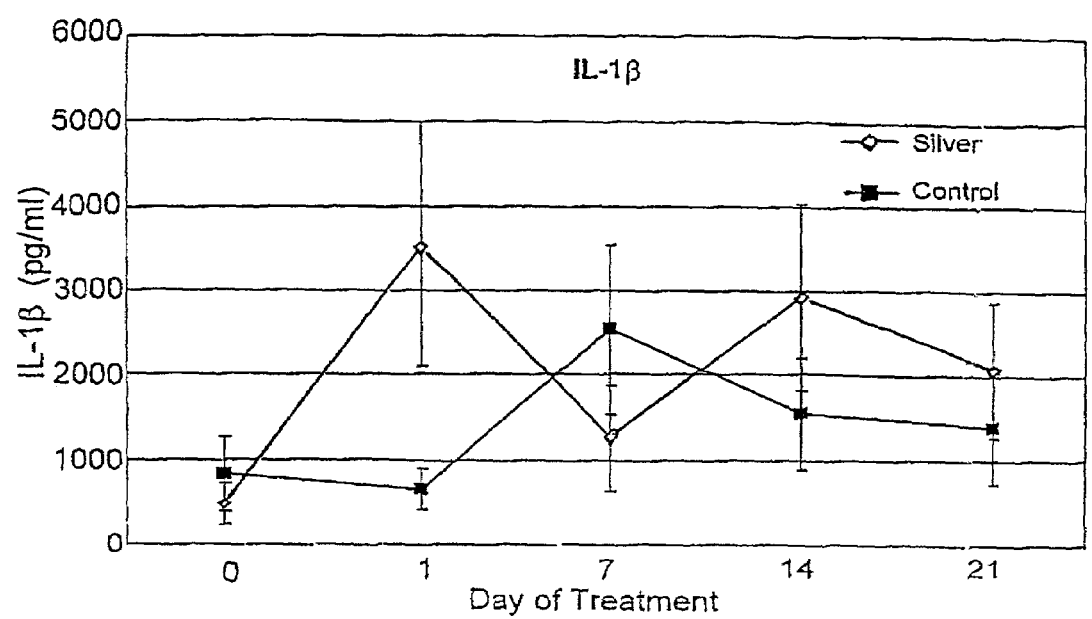
FIG. 6 is a graph showing the concentrations (pg/ml) of IL-1$\beta$ in fluid samples recovered from ulcers dressed with silver-coated dressing (Silver) and control dressing (Control) at days 0, 1, 7, 14 and 21.

FIG. 6 is a graph showing the concentrations (pg/ml) of IL-1β in fluid samples recovered from ulcers dressed with silver-coated dressing (Silver) and control dressing (Control) at days 0, 1, 7, 14 and 21. The levels of IL-1β were not significantly different with the silver-coated dressing and the control dressing.

The study suggests that the modulation of the MMP-9 and TNF-α levels is responsible for improved wound healing and reduced inflammation with silver-coated dressings. In comparison, the levels of MMPs and cytokines did not decrease over time with the control dressings.

This example and Example 4 above, taken together with the evidence that the silver materials herein disclosed are capable of reducing inflammation (see co-pending U.S. patent application Ser. No. 10/131,568, filed on Apr. 23, 2002; Ser. No. 10/131,511, filed on Apr. 23, 2002; Ser. No. 10/131,509, filed on Apr. 23, 2002; Ser. No. 10/131,513, filed on Apr. 23, 2002, which is now U.S. Patent No. 6,723,350; and Ser. No. 10/128,208 filed Apr. 23, 2002; and co-pending U.S. patent application Ser. No. 09/840,637 filed Apr. 23, 2001, and U.S. Provisional Patent Application No. 60/285,884 filed Apr. 23, 2001) demonstrates a method of reducing inflammation in a patient in need thereof, by contacting an area of inflammation or an inflammatory cell with a therapeutically effective amount of the antimicrobial metals in a crystalline form. The antimicrobial metals are characterized by sufficient atomic disorder, such that the metal, in contact with an alcohol or water-based electrolyte, releases atoms, ions, molecules, or clusters of at least one antimicrobial metal at a concentration sufficient to modulate the release of one or both of MMP-9 and TNF-α. Excessive TNF production has been reported in diseases, such as cancer and autoimmune diseases, which are characterized by elevated MMP activity. In this regard, use of the nanocrystalline silver of the present invention, when in therapeutically effective amounts, provides the dual modulation of MMP-9 and TNF-α to alleviate the particular condition.

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

We claim:

1. A method of treating excessive release of one or more matrix metalloproteinases from an inflammatory cell in a disease condition in a human or an animal, which comprises:
contacting the cell with a therapeutically effective amount of a noble metal in a crystalline form characterized by atomic disorder, or with a solution derived therefrom, to provide a modulating effect on one or more matrix metalloproteinases, wherein the noble metal is formed with sufficient atomic disorder, such that the metal, in contact with an alcohol or water-based electrolyte, releases atoms, ions, molecules, or clusters of at least one noble metal at a concentration sufficient to provide a localized anti-MMP effect.

2. The method according to claim 1, further comprising providing a modulating effect on one or more cytokines.

3. The method as set forth in claim 2, wherein the noble metal is silver.

4. The method as set forth in claim 3, wherein the noble metal is nanocrystalline and is formed with sufficient atomic disorder such that, in contact with an alcohol or water based electrolyte, the noble metal releases ions, atoms, molecules or clusters of the noble metal on a sustainable basis.

5. The method as set forth in claim 4, wherein the one or more matrix metalloproteinases are selected from the group consisting of collagenases, gelatinases, stromelysins, and stromelysin-like matrix metalloproteinases.

6. The method as set forth in claim 5, wherein the one or more matrix metalloproteinases is a gelatinase.

7. The method as set forth in claim 6, wherein the gelatinase is MMP-9.

8. The method as set forth in claim 7, wherein the cytokine is TNF-α.

9. The method as set forth in claim 8, wherein the noble metal is nanocrystalline silver.

10. The method as set forth in claim 8, wherein the noble metal is silver, formed as a composite with oxygen.

11. The method as set forth in claim 8, wherein the one or more noble metals are provided as a coating on, or filler in, a dressing or a hydrated dressing, or in a pharmaceutical composition with one or more pharmaceutically and dermatogically acceptable carriers, diluents, or excipients suitable for topical application.

12. The method as set forth in claim 11, wherein the pharmaceutical composition includes a nanocrystalline powder of one or more noble metals, or a solution containing dissolved species from a nanocrystalline powder or coating of one or more noble metals.

13. The method as set forth in claim 12, wherein the pharmaceutical composition is a gel, cream, lotion, paste, or ointment containing the noble metal powder in an amount of 0.01–10% by weight, or a liquid formulated as a topical solution, spray, mist, drops, infusion or instillation containing 0.001–10% by weight of the noble metal.

14. The method as set forth in claim 12, wherein the noble metal is nanocrystalline silver.

15. The method as set forth in claim 12, wherein the noble metal is silver, formed as a composite with oxygen.

16. The method as set forth in claim 12, wherein the noble metal is in a powder form and is delivered directly to a locus of the disease condition.

17. The method of claim 16, wherein the powder is sized with particulates no larger than 2 μm.

18. The method of claim 16, wherein the powder is sized with particulates no larger than 1 μm.

19. The method of claim 18, wherein the noble metal is nanocrystalline silver.

20. The method of claim 18, wherein the noble metal is nanocrystalline silver, formed as a composite with oxygen.

21. A method of treating excessive release of one or more matrix metalloproteinases from an inflammatory cell in a disease condition in a human or an animal, which comprises:
contacting the cell with a therapeutically effective amount of an antimicrobial metal in a crystalline form characterized by atomic disorder, or with a solution derived therefrom, to provide a modulating effect on one or more matrix metalloproteinases, wherein the antimicrobial metal is formed with sufficient atomic disorder, such that the metal, in contact with an alcohol or water-based electrolyte, releases atoms, ions, molecules, or clusters of at least one antimicrobial metal at a concentration sufficient to provide a localized anti-MMP effect.

22. The method according to claim 21, further comprising providing a modulating effect on one or more cytokines.

23. The method as set forth in claim 22, wherein the antimicrobial metal is silver.

24. The method as set forth in claim 23, wherein the antimicrobial metal is nanocrystalline and is formed with sufficient atomic disorder such that, in contact with an alcohol or water based electrolyte, the antimicrobial metal releases ions, atoms, molecules or clusters of the antimicrobial metal on a sustainable basis.

25. The method as set forth in claim 24, wherein the one or more matrix metalloproteinases are selected from the group consisting of collagenases, gelatinases, stromelysins, and stromelysin-like matrix metalloproteinases.

26. The method as set forth in claim 25, wherein the one or more matrix metalloproteinases is a gelatinase.

27. The method as set forth in claim 26, wherein the gelatinase is MMP-9.

28. The method as set forth in claim 27, wherein the cytokine is TNF-α.

29. The method as set forth in claim 28, wherein the antimicrobial metal is nanocrystalline silver.

30. The method as set forth in claim 28, wherein the antimicrobial metal is silver, formed as a composite with oxygen.

31. The method as set forth in claim 28, wherein the one or more antimicrobial metals are provided as a coating on, or filler in, a dressing or a hydrated dressing, or in a pharmaceutical composition with one or more pharmaceutically and dermatogically acceptable carriers, diluents, or excipients suitable for topical application.

32. The method as set forth in claim 31, wherein the pharmaceutical composition includes a nanocrystalline powder of one or more antimicrobial metals, or a solution containing dissolved species from a nanocrystalline powder or coating of one or more antimicrobial metals.

33. The method as set forth in claim 32, wherein the pharmaceutical composition is a gel, cream, lotion, paste, or ointment containing the antimicrobial metal powder in an amount of 0.01–10% by weight, or a liquid formulated as a topical solution, spray, mist, drops, infusion or instillation containing 0.001–10% by weight of the antimicrobial metal.

34. The method as set forth in claim 32, wherein the antimicrobial metal is nanocrystalline silver.

35. The method as set forth in claim 32, wherein the antimicrobial metal is silver, formed as a composite with oxygen.

36. The method as set forth in claim 32, wherein the antimicrobial metal is in a powder form and is delivered directly to a locus of the disease condition.

37. The method of claim 36, wherein the powder is sized with particulates no larger than 2 µm.

38. The method of claim 36, wherein the powder is sized with particulates no larger than 1 µm.

39. The method of claim 38, wherein the antimicrobial metal is nanocrystalline silver.

40. The method of claim 38, wherein the antimicrobial metal is nanocrystalline silver, formed as a composite with oxygen.

* * * * *

UNITED STATES PATENT AND TRADEMARK OFFICE
CERTIFICATE OF CORRECTION

PATENT NO. : 7,001,617 B2 Page 1 of 1
DATED : February 21, 2006
INVENTOR(S) : Robert E. Burrell, John B. Wright and Kan Lam It is certified that error appears in the above-identified patent and that said Letters Patent is hereby corrected as shown below:

Title page,
Item [73], Assignee, replace with the following:
-- Nucryst Pharmaceuticals Corp., Fort Saskatchewan, Alberta, Canada --.

Signed and Sealed this

Twenty-third Day of May, 2006

JON W. DUDAS
*Director of the United States Patent and Trademark Office*